United States Patent
Sherman

(10) Patent No.: US 9,919,030 B2
(45) Date of Patent: Mar. 20, 2018

(54) FOLLISTATIN FUSION PROTEINS AND USES THEREOF

(71) Applicant: Acceleron Pharma Inc., Cambridge, MA (US)

(72) Inventor: Matthew L. Sherman, Newton, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 14/622,459

(22) Filed: Feb. 13, 2015

(65) Prior Publication Data

US 2015/0158923 A1    Jun. 11, 2015

Related U.S. Application Data

(63) Continuation of application No. 12/459,205, filed on Jun. 26, 2009, now abandoned.

(60) Provisional application No. 61/133,354, filed on Jun. 26, 2008.

(51) Int. Cl.
| | | |
|---|---|---|
| C07K 14/475 | (2006.01) | |
| A61K 38/17 | (2006.01) | |
| C07K 14/72 | (2006.01) | |
| G01N 33/72 | (2006.01) | |
| G01N 33/80 | (2006.01) | |
| G01N 33/90 | (2006.01) | |
| A61K 38/22 | (2006.01) | |

(52) U.S. Cl.
CPC .......... *A61K 38/1796* (2013.01); *A61K 38/22* (2013.01); *C07K 14/475* (2013.01); *C07K 14/72* (2013.01); *G01N 33/721* (2013.01); *G01N 33/80* (2013.01); *G01N 33/90* (2013.01); *C07K 2319/30* (2013.01); *G01N 2333/47* (2013.01); *G01N 2333/79* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,041,538 A | 8/1991 | Ling et al. | |
| 5,182,375 A | 1/1993 | Ling et al. | |
| 5,545,616 A | 8/1996 | Woodruff | |
| 5,654,404 A | 8/1997 | Roos et al. | |
| 6,004,937 A | 12/1999 | Wood et al. | |
| 6,599,876 B2 | 7/2003 | Kojima | |
| 6,686,198 B1 | 2/2004 | Melton et al. | |
| 7,264,968 B2 | 9/2007 | Melton et al. | |
| 8,895,016 B2* | 11/2014 | Sherman | C07K 14/71 424/185.1 |
| 8,895,309 B2 | 11/2014 | Kaspar et al. | |
| 8,956,608 B2 | 2/2015 | Walsh et al. | |
| 2003/0162714 A1 | 8/2003 | Hill et al. | |
| 2004/0209805 A1 | 10/2004 | Phillips et al. | |
| 2007/0135336 A1 | 6/2007 | De Kretser et al. | |
| 2007/0149458 A1 | 6/2007 | Han et al. | |
| 2007/0248609 A1 | 10/2007 | De Kretser et al. | |
| 2010/0028331 A1* | 2/2010 | Sherman | C07K 14/71 424/130.1 |
| 2010/0028332 A1* | 2/2010 | Sherman | C07K 14/71 424/130.1 |
| 2010/0061997 A1 | 3/2010 | Lee et al. | |
| 2010/0286374 A1 | 11/2010 | Kannan et al. | |
| 2012/0003218 A1* | 1/2012 | Sherman | C07K 14/71 424/133.1 |
| 2012/0149876 A1 | 6/2012 | Von Kreudenstein et al. | |
| 2015/0023981 A1 | 1/2015 | De Kretser et al. | |
| 2015/0158923 A1 | 6/2015 | Sherman et al. | |
| 2015/0183845 A1* | 7/2015 | Sherman | C07K 14/71 424/134.1 |
| 2016/0185836 A1 | 6/2016 | Kumar et al. | |
| 2016/0256526 A1 | 9/2016 | Kumar et al. | |
| 2016/0311874 A1 | 10/2016 | Kumar et al. | |

FOREIGN PATENT DOCUMENTS

| | | |
|---|---|---|
| EP | 1174149 A1 | 1/2002 |
| WO | WO-1994006456 A1 | 3/1994 |
| WO | WO-1995/10611 A1 | 4/1995 |
| WO | WO-9715321 A1 | 5/1997 |
| WO | WO-1999/06559 A1 | 2/1999 |
| WO | WO-9945949 A2 | 9/1999 |
| WO | WO-2001009368 | 2/2001 |
| WO | WO-02/10214 | 2/2002 |
| WO | WO-2002/085306 A2 | 10/2002 |
| WO | WO-2003/006057 A1 | 1/2003 |
| WO | WO-03072714 | 9/2003 |
| WO | WO-2004082710 A1 | 9/2004 |
| WO | WO-2004/108157 A2 | 12/2004 |
| WO | WO-2005025601 A1 | 3/2005 |
| WO | WO-2005032578 A1 | 4/2005 |
| WO | WO-2005033134 A2 | 4/2005 |

(Continued)

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Gonzalez (Proc Natl Acad Sci U S A. Jan. 25, 2005;102(4):1116-21. Epub Jan. 12, 2005).*
Alignment of human follistatin with EMBOSS Needle performed Oct. 14, 2016 at http://www.ebi.ac.uk/Tools/psa/emboss_needle/).*
Shimasaki et al (Proc Natl Acad Sci U S A. Jun. 1988;85(12):4218-22).*
Sahin et al (Encyclopedia of Cancer Jun. 1, 2015; pp. 1-4).*
Borgnon et al, "Follistatin Allows Efficient Retroviral-Mediated Gene Transfer into Rat Liver," Biochemical and Biophysical Research Communications 328; pp. 937-943 (2005).

(Continued)

*Primary Examiner* — Brian Gangle
*Assistant Examiner* — Andrea K McCollum
(74) *Attorney, Agent, or Firm* — White & Case LLP

(57) ABSTRACT

In certain aspects, the present invention provides methods for dosing a patient with a follistatin antagonist and methods for managing patients treated with a follistatin antagonist.

23 Claims, 1 Drawing Sheet

(56) References Cited

FOREIGN PATENT DOCUMENTS

| WO | WO-2005100563 A1 | 10/2005 |
| WO | WO-2006/020884 A2 | 2/2006 |
| WO | WO-2006083182 A1 | 8/2006 |
| WO | WO-2007/067616 A2 | 6/2007 |
| WO | WO-2008030367 A2 | 3/2008 |
| WO | WO-2009/158025 A2 | 12/2009 |
| WO | WO-2009158035 A2 | 12/2009 |
| WO | WO-2013/151665 A2 | 10/2013 |
| WO | WO-2013170315 A1 | 11/2013 |
| WO | WO-2014116981 A1 | 7/2014 |
| WO | WO-2014187807 A1 | 11/2014 |
| WO | WO-2015/187977 A1 | 12/2015 |

OTHER PUBLICATIONS

Datta-Mannan A. et al. "An Engineered Human Follistatin Variant: Insights into the Pharmacokinetic and Pharmocodynamic Relationships of a Novel Molecule with Broad Therapeutic Potential" The Journal of Pharmacology and Experimental Therapeutics (2013) 344 (3): 616-623.

Takabe et al, "AdenovirMediated Overexpression of Follistatin Enlarges Intact Liver of Adult Rats," Hepatology, vol. 38, No. 5 pp. 1107-1115 (2003).

Yaden B. C. et al. "Follistatin: A Novel Therapeutic for the Improvement of Muscle Regeneration" The Journal of Pharmacology and Experimental Therapeutics (2014) 349 (2): 355-371.

Brenner, "Errors in genome annotation," Trends in Genetics, vol. 15(4): 132-133 (1999).

Cash et al., "Characterization of Follistatin-Type Domains and Their Contribution to Myostatin and Activin A Antagonism," Mol. Endocrinol. vol. 26(7): 1167-1178 (2012).

Doerks et al., "Protein annotation: detective work for function prediction," Trends in Genetics, vol. 14(6): 248-250 (1998).

Klein et al., "Progress in overcoming the chain association issue in bispecific heterodimeric IgG antibodies," mAbs., vol. 4(6): 653-663 (2012).

Lin et al., "Regulation of ovarian functions by the TGF-β superfamily and follistatin," Reproduction, vol. 126: 133-148 (2003).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433-440 and 492-495 (1994).

Skolnick and Fetrow, "From Genes to protein structure and function: novel applications of computational approaches in the genomic era," Trends in Biotech. vol. 18(1): 34-39 (2000).

Sugino et al., "Molecular Heterogeneity of Follistatin, an Activin-binding Protein," The Journal of Biological Chemistry, vol. 268(21): 15579-15587 (1993).

Wells, J.A., "Additivity of Mutational Effects in Proteins," Biochemistry, 29(37):8509-8517 (1990).

Ying, "Inhibins, Activins, and Follistatins: Gonadal Proteins Modulating the Secretion of Follicle-Stimulating Hormone," Endocrine Reviews, vol. 9(2): 267-293 (1998).

Datta-Mannan et al, "Insights into the Impact of Heterogeneous Glycosylation on the Pharmacokinetic Behavior of Follistatin-Fc-Based Biotherapeutics", Drug Metabolism & Disposition, 43(12), pp. 1882-1890 (Dec. 2015).

Foley et al, "Evaluation of Systemic Follistatin as an Adjuvant to Stimulate Muscle Repair and Improve Motor Function in Pompe Mice," Molecular Therapy, vol. 18, No. 9 pp. 1584-1591 (Sep. 2010).

Guo et al, "Overexpression of Mouse Follistatin Causes Reproductive Defects in Transgenic Mice," Molecular Endocrinology, vol. 12 No. 1, 11 pages (1998).

Haidet et al, "Long-term Enhancement of Skeletal Muscle Mass and Strength by Single Gene Administration of Myostatin Inhibitors," PNAS, vol. 105, No. 11, pp. 4318-4322, (Mar. 18, 2008).

Inouye et al, "Recombinant Expression of Human Follistatin with 315 and 288 Amino Acids: Chemical and Biological Comparison with Native Porcine Follistatin," Endocrinology, vol. 129, No. 2, pp. 815-822, (1991).

Kota et al, "Follistatin Gene Delivery Enhances Muscle Growth and Strength in Nonhuman Primates," Sci Transl Med. 17 pages (Nov. 2009).

Miller et al, "Gene Transfer Demonstrates that Muscle is not a Primary Target for Non-cell-autonomous Toxicity in Familial Amyotrophic Lateral Sclerosis," PNAS, vol. 103, No. 51, pp. 19546-19551 (Dec. 19, 2006).

Nakatani et al, "Transgenic Expression of a Myostatin Inhibitor Derived from Follistatin Increases Skeletal Muscle Mass and Ameliorates Dystrophic Pathology in mdx Mice," The FASEB Journal, vol. 22, pp. 477-487 (Feb. 2008).

Rodino-Klapac et al, "Inhibition of Myostatin with Emphasis on Follistatin as a Therapy for Muscle Disease," Muscle Nerve, Mar;39(3) 22 pages (Mar. 2009).

Rose et al, "Delivery of Recombinant Follistatin Lessens Disease Severity in a Mouse Model of Spinal Muscular Atrophy," Human Molecular Genetics, vol. 18, No. 6, pp. 997-1005 (Dec. 12, 2008).

Sidis et al, "Heparin and Activin-Binding Determinants in Follistatin and FSTL3," Endocrinology, 146(1): pp. 130-136 (Jan. 2005).

Takabe et al, "Adenovirus-Mediated Overexpression of Follistatin Enlarges Intact Liver of Adult Rats," Hepatology, vol. 38, No. 5 pp. 1107-1115 (2003).

Tilbrook et al, "Human Recombinant Follistatin-288 Suppresses Plasma Concentrations of Follicle-Stimulating Hormone But is Not a Significant Regulator of Luteinizing Hormone in Castrated Rams," Biology of Reproduction, pp. 1353-1358 (1995).

Wang et al., "Analysis of Human Follistatin Structure: Identification of Two Discontinuous N-Terminal Sequences Coding for Activin A Binding and Structural Conseuqences of Activin Binding to Native Proteins," Endocrinology, vol. 141(9): 3183-3193 (2000).

Zhu et al, "Follistatin Improves Skeletal Muscle Healing after Injury Disease through an Interaction with Muscle Regeneration, Angiogenesis, and Fibrosis," The American Journal of Pathology, vol. 179, No. 2, pp. 915-930 (Aug. 2011).

\* cited by examiner

```
ActRIIa    ILGRSETQEC  LFFNANWEKD  RTNQTGVEPC  YGDKDKRRHC  FATWKNISGS
ActRIIb    GRGEAETREC  IYYNANWELE  RTNQSGLERC  EGEQDKRLHC  YASWRNSSGT

IEIVKQGCWL  DDINCYDRTD  CVEKKDSPEV  YFCCCEGNMC  NEKFSYFPEM
           IELVKKGCWL  DDFNCYDRQE  CVATEENPQV  YFCCCEGNFC  NERFTHLPEA

EVTQPTSNPV  TPKPPT
           GGPEVTYEPP  PTAPT
```

FOLLISTATIN FUSION PROTEINS AND USES THEREOF

RELATED APPLICATIONS

This application is a continuation of U.S. application Ser. No. 12/459,205, filed Jun. 26, 2009, which claims the benefit of U.S. Provisional Application No. 61/133,354, filed on Jun. 26, 2008 The specifications of each of the foregoing applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 13, 2015, is named PHPH048102_Seq.txt and is 35,626 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP 10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Changes in muscle, bone, cartilage and other tissues may be achieved by agonizing or antagonizing signaling that is mediated by an appropriate TGF-beta family member. It is an object of the present disclosure to provide alternative methods for administering modulators of the TGF-beta superfamily to patients.

SUMMARY OF THE INVENTION

In part, the disclosure related to methods for administering ActRIIB antagonists to patients in a manner that is appropriate given the effects that such antagonists can have on a variety of tissues, including red blood cells. In some embodiments, the disclosure provides ActRIIb antagonists can increase red blood cell and hemoglobin levels and also promote muscle growth or bone growth. This dual effect has particular advantages in patients that have both anemia and muscle or bone loss, such as many cancer patients (where anemia and muscle loss can be a consequence of the tumor or a consequence of irradiation or chemotherapy), many forms of cachexia, sarcopenia (muscle loss associated with aging). In particular, the disclosure demonstrates that a soluble form of ActRIIb is effective to increase reticulocyte levels in vivo, an effect which over a longer time period is expected to cause increased hematocrit levels. While soluble ActRIIb may affect reticulocyte levels through a mechanism other than ActRIIb antagonism, the disclosure nonetheless demonstrates that desirable therapeutic agents may be selected on the basis of ActRIIb antagonism. The term ActRIIb antagonist is used herein to indicate soluble ActRIIb polypeptides (e.g., ActRIIb-Fc), as well as antibodies and other antagonists that target ActRIIb or its ligands at the protein or nucleic acid level. As described herein, and in published patent applications WO/2009/038745, WO/2008/100384, WO/2008/094708, WO/2008/076437, WO/2007/062188 and WO/2006/012627, ActRIIb antagonists also have a variety of other therapeutic uses including, for example, promoting bone growth, or promoting muscle growth. In certain instances, when administering an ActRIIb antagonist for promoting bone growth growth or promoting muscle growth, it may be desirable to monitor the effects on red blood cells during administration of an ActRIIb antagonist, or to determine or adjust the dosing of an ActRIIb antagonist, in order to reduce undesired effects on red blood cells. For example, excessive increases in red blood cell levels, hemoglobin levels, or hematocrit levels may cause increases in blood pressure or other undesirable side effects. It may also be desirable to restrict dosing of ActRIIb antagonists to patients who have appropriate hematologic parameters. For example, it may be desirable to limit dosing to only those patients who have a hemoglobin level below normal (e.g., below 12 g/dL, below 11 g/dL, below 10 g/dL or below 9 g/dL or lower).

Therefore, in certain embodiments, the disclosure provides methods for managing a patient that has been treated with, or is a candidate to be treated with, an ActRIIb-antagonist, including, for example, ActRIIb polypeptides (including those that bind to one or more ActRIIb ligands such as activin or myostatin), anti-ActRIIb antibodies, or ActRIIb-targeted small molecules and aptamers, and nucleic acids that decrease expression of ActRIIb, by monitoring in the patient one or more hematologic parameters that correlate with an increase in red blood cell levels, such as, for example, red blood cell levels, blood pressure, or iron stores.

In certain aspects, the disclosure provides polypeptides comprising a soluble, ligand-binding ActRIIb polypeptide that binds to activin or myostatin or other ActRIIb ligand. ActRIIb polypeptides may be formulated as a pharmaceutical preparation comprising the ligand-binding (e.g. activin-binding) ActRIIb polypeptide and a pharmaceutically acceptable carrier. The ligand-binding ActRIIb polypeptide may bind to activin with a $K_D$ less than 1 micromolar or less than 100, 10 or 1 nanomolar. The composition may be at least 95% pure, with respect to other polypeptide components, as assessed by size exclusion chromatography, and optionally, the composition is at least 98% pure. An ActRIIb polypeptide for use in such a preparation may be any of those disclosed herein, such as a polypeptide having an amino acid sequence selected from SEQ ID NOs: 2, 3, 6, 8, or 9 or having an amino acid sequence that is at least 80%, 85%, 90%, 95%, 97% or 99% identical to an amino acid sequence selected from SEQ ID NOs: 2, 3, 6, 8, or 9. An active ActRIIb polypeptide may include a functional fragment of a natural ActRIIb polypeptide, such as one comprising at least 10, 20 or 30 amino acids of SEQ ID NOs: 1-3 or a sequence lacking the C-terminal 10 to 15 amino acids (the "tail") such as SEQ ID NO: 3.

A soluble, ligand-binding (e.g., activin-binding) ActRIIb polypeptide may include one or more alterations in the amino acid sequence (e.g., in the ligand-binding domain) relative to a naturally occurring ActRIIb polypeptide. Examples of altered ActRIIb polypeptides are provided in WO 2006/012627, pp. 59-60 and pp. 55-58, respectively, which are incorporated by reference herein, and throughout U.S. patent application Ser. No. 12/012,652, incorporated by reference herein. The alteration in the amino acid sequence may, for example, alter glycosylation of the polypeptide when produced in a mammalian, insect or other eukaryotic cell or alter proteolytic cleavage of the polypeptide relative to the naturally occurring ActRIIb polypeptide.

A ligand-binding (e.g., activin-binding) ActRIIb polypeptide may be a fusion protein that has, as one domain, an ActRIIb polypeptide, (e.g., a ligand-binding portion of an ActRIIb) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. A ligand-binding ActRIIb fusion protein may include an immunoglobulin Fc domain (wild-type or mutant) or a serum albumin or other polypeptide portion that provides desirable properties such as improved pharmacokinetics, improved solubility or improved stability. In a preferred embodiment, an ActRIIb-Fc fusion comprises a relatively unstructured linker positioned between the Fc domain and the extracellular ActRIIb domain. This unstructured linker may be an artificial sequence of 1, 2, 3, 4 or 5 amino acids or a length of between 5 and 15, 20, 30, 50 or more amino acids that are relatively free of secondary structure, or a mixture of both. A linker may be rich in glycine and proline residues and may, for example, contain a single sequence of threonine/serine and glycines or repeating sequences of threonine/serine and glycines (e.g., $TG_4$ (SEQ ID NO: 14) or $SG_4$ (SEQ ID NO: 15) singlets or repeats). A fusion protein may include a purification subsequence, such as an epitope tag, a FLAG tag, a polyhistidine sequence, and a GST fusion. Optionally, a soluble ActRIIb polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a bone disorder or a compound that is used to treat anemia. Preferably, a pharmaceutical preparation is substantially pyrogen free. In general, it is preferable that an ActRIIb protein be expressed in a mammalian cell line that mediates suitably natural glycosylation of the ActRIIb protein so as to diminish the likelihood of an unfavorable immune response in a patient. Human and CHO cell lines have been used successfully, and it is expected that other common mammalian expression systems will be useful.

In some embodiments, ActRIIb proteins designated ActRIIb-Fc have specific properties, including selective binding to activin versus GDF8 and/or GDF11 or vice versa, high affinity ligand binding and serum half life greater than two weeks in animal models and in human patients. In certain embodiments the invention provides ActRIIb-Fc polypeptides and pharmaceutical preparations comprising such polypeptides and a pharmaceutically acceptable excipient.

In certain aspects, the disclosure provides nucleic acids encoding a soluble ligand-binding ActRIIb polypeptide. An isolated polynucleotide may comprise a coding sequence for a soluble, ligand-binding (e.g. activin-binding) ActRIIb polypeptide, such as described above. For example, an isolated nucleic acid may include a sequence coding for an extracellular domain (e.g., ligand-binding domain) of an ActRIIb and a sequence that would code for part or all of the transmembrane domain and/or the cytoplasmic domain of an ActRIIb, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIb polynucleotide sequence such as SEQ ID NO: 4 or a partially truncated version of ActRIIb, such as a nucleic acid comprising the nucleic acid sequence of SEQ ID NO: 5, which corresponds to the extracellular domain of ActRIIb. An isolated polynucleotide may further comprise a transcription termination codon at least six hundred nucleotides before the 3'-terminus or otherwise positioned such that translation of the polynucleotide gives rise to an extracellular domain optionally fused to a truncated portion of a full-length ActRIIb. A preferred nucleic acid sequence for ActRIIb is SEQ ID NO: 10. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble, ligand-binding (e.g. activin-binding) ActRIIb polypeptide. Such a method may include expressing any of the nucleic acids (e.g., SEQ ID NOs: 4, 5, or 10) disclosed herein in a suitable cell, such as a Chinese hamster ovary (CHO) cell or a human cell. Such a method may comprise: a) culturing a cell under conditions suitable for expression of the soluble ActRIIb polypeptide, wherein said cell is transformed with a soluble ActRIIb expression construct; and b) recovering the soluble ActRIIb polypeptide so expressed. Soluble ActRIIb polypeptides may be recovered as crude, partially purified or highly purified fractions. Purification may be achieved by a series of purification steps, including, for example, one, two or three or more of the following, in any order: protein A chromatography, anion exchange chromatography (e.g., Q SEPHAROSE® (a cross-linked beaded form of agarose)), hydrophobic interaction chromatography (e.g., phenylsepharose), size exclusion chromatography, and cation exchange chromatography. Soluble ActRIIb polypeptides may be formulated in liquid or solid (e.g., lyophilized) forms.

In certain aspects, the disclosure provides a method for dosing a patient with an activin-ActRIIb antagonist, comprising dosing the patient in amounts and at intervals selected so as to reduce the risk of causing a rise in hemoglobin levels greater than 0.5 g/dL, 1 g/dl or 1.5 g/dL in two weeks.

In certain aspects, the disclosure provides a method for administering an ActRIIb-Fc fusion protein to a patient, comprising administering the ActRIIb fusion protein no more frequently than once per 60 days, once per 90 days, or once per 120 days. In certain embodiments, the patient may be a patient in need of bone growth or muscle growth.

BRIEF DESCRIPTION OF THE DRAWINGS

FIG. 1 shows an alignment of human ActRIIA (SEQ ID NO: 24) and ActRIIB (SEQ ID NO: 25) with the residues that are deduced herein, based on composite analysis of multiple ActRIIB and ActRIIA crystal structures to directly contact ligand (the ligand pocket) indicated with boxes.

DETAILED DESCRIPTION OF THE INVENTION

1. Overview

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP 10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Activins are dimeric polypeptide growth factors that belong to the TGF-beta superfamily. There are three principal activin forms (A, B, and AB) that are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP) and $\alpha_2$-macroglobulin.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors (ActRII), ActRIIa and ActRIIb, have been identified as the type II receptors for activins (Mathews and Vale, 1991, Cell 65:973-982; Attisano et al., 1992, Cell 68: 97-108). Besides activins, ActRIIa and ActRIIb can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

As demonstrated herein, a soluble ActRIIb polypeptide (sActRIIb) is effective to increase reticulocyte levels in vivo, an effect which, over a longer time period is expected to cause increased hematocrit levels. Increases were observed in rodents with longer exposure. Thus, in some embodiments, sActRIIb polypeptides of the disclosure may be used increase red blood cell levels in vivo. Regardless of mechanism, it is apparent from this disclosure that ActRIIb antagonists stimulate erythropoiesis in rodents and monkeys. It should be noted that hematopoiesis is a complex process, regulated by a variety of factors, including erythropoietin, G-CSF and iron homeostasis. The terms "increase red blood cell levels" and "promote red blood cell formation" refer to clinically observable metrics, such as hematocrit, red blood cell counts and hemoglobin measurements, and are intended to be neutral as to the mechanism by which such changes occur.

In addition to stimulating red blood cell levels, certain ActRIIb antagonists are useful for a variety of therapeutic applications, including, for example, promoting bone growth (see PCT Publication WO 2006/012627, which is hereby incorporated by reference in its entirety) and promoting muscle growth (see PCT Publication No. WO2006/012627 and PCT Application No. PCT/US2008/001506, which are hereby incorporated by reference in their entirety). In certain instances, when administering an ActRIIb antagonist for the purpose of increasing muscle or bone, it may be desirable to reduce or minimize or otherwise monitor effects on red blood cells. In some instances, a dual effect on blood cells and muscle, bone or other tissue will be desirable, but it is generally recognized that pharmaceutically promoted increases in red blood cells, even up to a level that is typically considered normal, can have adverse effects on patients, and thus are often monitored or managed with care. By monitoring various hematologic parameters in patients being treated with, or who are candidates for treatment with, an ActRIIb antagonist, appropriate dosing (including amounts and frequency of administration) may be determined based on an individual patient's needs, baseline hematologic parameters, and purpose for treatment. Furthermore, therapeutic progress and effects on one or more hematologic parameters over time may be useful in managing patients being dosed with an ActRIIb antagonist by facilitating patient care, determining appropriate maintenance dosing (both amounts and frequency), etc.

ActRIIb antagonists include, for example, ligand-binding (e.g. activin-binding) soluble ActRIIb polypeptides, antibodies that bind to ActRIIb and disrupt activin binding, non-antibody proteins selected for ActRIIb binding (see e.g., WO/2002/088171, WO/2006/055689, and WO/2002/032925 for examples of such proteins and methods for design and selection of same), randomized peptides selected for ActRIIb binding, often affixed to an Fc domain. Two different proteins (or other moieties) with ActRIIb binding activity may be linked together to create a bifunctional binding molecule. Nucleic acid aptamers, small molecules and other agents that inhibit the ActRIIb signaling axis are included as ActRIIb antagonists. Various proteins have antagonist that may be similar to ActRIIb antagonists, including inhibin (i.e., inhibin alpha subunit), although inhibin does not universally antagonize activin in all tissues, follistatin (e.g., follistatin-288 and follistatin-315), FSRP, FLRG, activin C, alpha(2)-macroglobulin, and an M108A (methionine to alanine change at position 108) mutant activin A. Generally, alternative forms of activin, particularly those with alterations in the type I receptor binding domain can bind to type II receptors and fail to form an active ternary complex, thus acting as antagonists. Additionally, nucleic acids, such as antisense molecules, siRNAs or ribozymes that inhibit ActRIIb expression, can be used as ActRIIb antagonists. The ActRIIb antagonist to be used may exhibit selectivity for inhibiting activin-mediated signaling versus other members of the TGF-beta family, and particularly with respect to GDF8 and GDF11.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST™ (Basic Local Alignment Search Tool), FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRIIb Polypeptides

In certain aspects, the present invention relates to ActRIIb polypeptides. As used herein, the term "ActRIIb" refers to a family of activin receptor type IIb (ActRIIb) proteins from any species and variants derived from such ActRIIb proteins by mutagenesis or other modification. Reference to ActRIIb herein is understood to be a reference to any one of the currently identified forms. Members of the ActRIIb family are generally transmembrane proteins, composed of a ligand-binding extracellular domain with a cysteine-rich region, a transmembrane domain, and a cytoplasmic domain with predicted serine/threonine kinase activity.

In certain aspects, the present invention relates to ActRIIb polypeptides. As used herein, the term "ActRIIb" refers to a family of activin receptor type IIb (ActRIIb) proteins from any species and variants derived from such ActRIIb proteins by mutagenesis or other modification. Reference to ActRIIb herein is understood to be a reference to any one of the currently identified forms. Members of the ActRIIb family are generally transmembrane proteins, composed of a ligand-binding extracellular domain with a cysteine-rich region, a transmembrane domain, and a cytoplasmic domain with predicted serine/threonine kinase activity.

The term "ActRIIb polypeptide" includes polypeptides comprising any naturally occurring polypeptide of an ActRIIb family member as well as any variants thereof (including mutants, fragments, fusions, and peptidomimetic forms) that retain a useful activity. See, for example, WO/2006/012627 and WO/2008/097541. For example, ActRIIb polypeptides include polypeptides derived from the sequence of any known ActRIIb having a sequence at least about 80% identical to the sequence of an ActRIIb polypeptide, and optionally at least 85%, 90%, 95%, 97%, 99% or greater identity. For example, an ActRIIb polypeptide of the invention may bind to and inhibit the function of an ActRIIb protein and/or activin. An ActRIIb polypeptide may be selected for activity in promoting red blood cell formation in vivo. Examples of ActRIIb polypeptides include human ActRIIb precursor polypeptide (SEQ ID NO: 1) and soluble human ActRIIb polypeptides (e.g., SEQ ID NO: 2, 3, 8, and 9).

The human ActRIIb precursor protein sequence is as follows:

(SEQ ID NO: 1)
MTAPWVALALLWGSLWPGSGRGEAETRECIYYNANWELERTNQSGLERCE

GEQDKRLHCYASWANSSGTIELVKKGCWLDDFNCYDRQECVATEENPQVY

FCCCEGNFCNERFTHLPEAGGPEVTYEPPPTAPTLLTVLAYSLLPIGGLS

LIVLLAFWMYRHRKPPYGHVDIHEDPGPPPPSPLVGLKPLQLLEIKARGR

FGCVWKAQLMNDFVAVKIFPLQDKQSWQSEREIFSTPGMKHENLLQFIAA

-continued
EKRGSNLEVELWLITAFHDKGSLTDYLKGNIITWNELCHVAETMSRGLSY

LHEDVPWCRGEGHKPSIAHRDFKSKNVLLKSDLTAVLADFGLAVRFEPGK

PPGDTHGQVGTRRYMAPEVLEGAINFQRDAFLRIDMYAMGLVLWELVSRC

KAADGPVDEYMLPFEEEIGQHPSLEELQEVVVHKKMRPTIKDHWLKHPGL

AQLCVTIEECWDHDAEARLSAGCVEERVSLIRRSVNGTTSDCLVSLVTSV

TNVDLPPKESSI

The signal peptide is single underlined; the extracellular domain is in bold and the potential N-linked glycosylation sites are in boxes.

The human ActRIIb soluble (extracellular), processed polypeptide sequence is as follows:

(SEQ ID NO: 2)
GRGEAETRECIYYNANWELERTNQSGLERCEGEQDKRLHCYASWANSSG

TIELVKKGCWLDDFNCYDRQECVATEENPQVYFCCCEGNFCNERFTHLP

EAGGPEVTYEPPPTAPT

In some conditions, the protein may be produced with an "SGR . . . " sequence at the N-terminus. The C-terminal "tail" of the extracellular domain is underlined. The sequence with the "tail" deleted (a Δ15 sequence) is as follows:

(SEQ ID NO: 3)
GRGEAETRECIYYNANWELERTNQSGLERCEGEQDKRLHCYASWANSSG

TIELVKKGCWLDDFNCYDRQECVATEENPQVYFCCCEGNFCNERFTHLP

EA

In some conditions, the protein may be produced with an "SGR . . . " sequence at the N-terminus. The nucleic acid sequence encoding a human ActRIIb precursor protein is as follows: (nucleotides 5-1543 of Genbank entry NM_001106)

(SEQ ID NO: 4)
ATGACGGCGCCCTGGGTGGCCCTCGCCCTCCTCTGGGGATCGCTGTGGC

CCGGCTCTGGGCGTGGGGAGGCTGAGACACGGGAGTGCATCTACTACAA

CGCCAACTGGGAGCTGGAGCGCACCAACCAGAGCGGCCTGGAGCGCTGC

GAAGGCGAGCAGGACAAGCGGCTGCACTGCTACGCCTCCTGGGCCAACA

GCTCTGGCACCATCGAGCTCGTGAAGAAGGGCTGCTGGCTAGATGACTT

CAACTGCTACGATAGGCAGGAGTGTGTGGCCACTGAGGAGAACCCCCAG

GTGTACTTCTGCTGCTGTGAAGGCAACTTCTGCAACGAGCGCTTCACTC

ATTTGCCAGAGGCTGGGGGCCCGGAAGTCACGTACGAGCCACCCCCGAC

AGCCCCCACCCTGCTCACGGTGCTGGCCTACTCACTGCTGCCCATCGGG

GGCCTTTCCCTCATCGTCCTGCTGGCCTTTTGGATGTACCGGCATCGCA

AGCCCCCCTACGGTCATGTGGACATCCATGAGGACCCTGGGCCTCCACC

ACCATCCCCTCTGGTGGGCCTGAAGCCACTGCAGCTGCTGGAGATCAAG

GCTCGGGGGCGCTTTGGCTGTGTCTGGAAGGCCCAGCTCATGAATGACT

TTGTAGCTGTCAAGATCTTCCCACTCCAGGACAAGCAGTCGTGGCAGAG

-continued
TGAACGGGAGATCTTCAGCACACCTGGCATGAAGCACGAGAACCTGCTA

CAGTTCATTGCTGCCGAGAAGCGAGGCTCCAACCTCGAAGTAGAGCTGT

GGCTCATCACGGCCTTCCATGACAAGGGCTCCCTCACGGATTACCTCAA

GGGGAACATCATCACATGGAACGAACTGTGTCATGTAGCAGAGACGATGT

CACGAGGCCTCTCATACCTGCATGAGGATGTGCCCTGGTGCCGTGGCGAG

GGCCACAAGCCGTCTATTGCCCACAGGGACTTTAAAAGTAAGAATGTATT

GCTGAAGAGCGACCTCACAGCCGTGCTGGCTGACTTTGGCTTGGCTGTTC

GATTTGAGCCAGGGAAACCTCCAGGGGACACCCACGGACAGGTAGGCAC

GAGACGGTACATGGCTCCTGAGGTGCTCGAGGGAGCCATCAACTTCCAG

AGAGATGCCTTCCTGCGCATTGACATGTATGCCATGGGGTTGGTGCTGT

GGGAGCTTGTGTCTCGCTGCAAGGCTGCAGACGGACCCGTGGATGAGTA

CATGCTGCCCTTTGAGGAAGAGATTGGCCAGCACCCTTCGTTGGAGGAG

CTGCAGGAGGTGGTGGTGCACAAGAAGATGAGGCCCACCATTAAAGATC

ACTGGTTGAAACACCCGGGCCTGGCCCAGCTTTGTGTGACCATCGAGGA

GTGCTGGGACCATGATGCAGAGGCTCGCTTGTCCGCGGGCTGTGTGGAG

GAGCGGGTGTCCCTGATTCGGAGGTCGGTCAACGGCACTACCTCGGACT

GTCTCGTTTCCCTGGTGACCTCTGTCACCAATGTGGACCTGCCCCCTAA

AGAGTCAAGCATCTAA

The nucleic acid sequence encoding a human ActRIIb soluble (extracellular) polypeptide is as follows:

(SEQ ID NO: 5)
TCTGGGCGTGGGGAGGCTGAGACACGGGAGTGCATCTACTACAACGCCAA

CTGGGAGCTGGAGCGCACCAACCAGAGCGGCCTGGAGCGCTGCGAAGGCG

AGCAGGACAAGCGGCTGCACTGCTACGCCTCCTGGGCCAACAGCTCTGGC

ACCATCGAGCTCGTGAAGAAGGGCTGCTGGCTAGATGACTTCAACTGCTA

CGATAGGCAGGAGTGTGTGGCCACTGAGGAGAACCCCCAGGTGTACTTCT

GCTGCTGTGAAGGCAACTTCTGCAACGAGCGCTTCACTCATTTGCCAGAG

GCTGGGGGCCCGGAAGTCACGTACGAGCCACCCCCGACAGCCCCCACC

In a specific embodiment, the invention relates to soluble ActRIIb polypeptides. As described herein, the term "soluble ActRIIb polypeptide" generally refers to polypeptides comprising an extracellular domain of an ActRIIb protein. The term "soluble ActRIIb polypeptide," as used herein, includes any naturally occurring extracellular domain of an ActRIIb protein as well as any variants thereof (including mutants, fragments and peptidomimetic forms). A ligand-binding (e.g. activin-binding) ActRIIb polypeptide is one that retains the ability to bind to activin, including, for example, activin AA, AB, BB, or forms that include a C or E subunit. Optionally, a ligand-binding (e.g. activin-binding) ActRIIb polypeptide will bind to activin AA with a dissociation constant of 1 nM or less. The extracellular domain of an ActRIIb protein binds to activin and other ligands, such as myostatin, and is generally soluble in physiological conditions, and thus can be termed a soluble, ligand-binding (e.g. activin-binding) ActRIIb polypeptide. Examples of soluble, ligand-binding (e.g. activin-binding) ActRIIb polypeptides include the soluble polypeptides illustrated in SEQ ID NOs: 2, 3, 8, and 9. SEQ ID NO: 8 is referred to as ActRIIb-hFc, and is described further in the Examples. Other examples of soluble, ligand-binding (e.g. activin-binding) ActRIIb polypeptides comprise a signal sequence in addition to the extracellular domain of an ActRIIb protein, for example, the honey bee mellitin leader sequence (SEQ ID NO: 11), the tissue plaminogen activator (TPA) leader (SEQ ID NO: 12) or the native ActRIIb leader (SEQ ID NO: 13). The ActRIIb-hFc polypeptide illustrated in SEQ ID NO: 9 uses a TPA leader.

Extensive analysis of structure function analysis of ActRIIb is provided in U.S. patent application Ser. No. 12/012,652, which analysis is incorporated by reference herein. FIG. 1 shows amino acids that are involved in the ligand binding domain. ActRIIb residues likely to be in contact with ligands in the binding pocket have been defined. At these positions, it is expected that conservative mutations will be tolerated, although a K74A mutation is well-tolerated, as are R40A, K55A, F82A and mutations at position L79. R40 is a K in Xenopus, indicating that basic amino acids at this position will be tolerated. Q53 is R in bovine ActRIIB and K in Xenopus ActRIIB, and therefore amino acids including R, K, Q, N and H will be tolerated at this position. Outside of these residues, it is expected that modifications will be relatively well-tolerated, provided that such alterations do not disrupt the structure of the protein as a whole. It is readily apparent when a protein structure is disrupted because the protein will tend to express poorly or be degraded in the culture media. Thus, a general formula for an active ActRIIb variant protein is one that comprises amino acids 12-82 of SEQ ID No. 2 respectively, but optionally beginning at a position ranging from 1-5 or 3-5 and ending at a position ranging from 110-116 or 110-115, respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may comprise an amino acid sequence that retains greater than 80%, 90%, 95% or 99% sequence identity to the sequence of amino acids 29-109 of SEQ ID NO: 2.

Functionally active fragments of ActRIIb polypeptides can be obtained by screening polypeptides recombinantly produced from the corresponding fragment of the nucleic acid encoding an ActRIIb polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIb protein or signaling mediated by activin.

Functionally active variants of ActRIIb polypeptides can be obtained by screening libraries of modified polypeptides recombinantly produced from the corresponding mutagenized nucleic acids encoding an ActRIIb polypeptide. The variants can be produced and tested to identify those that can function as antagonists (inhibitors) of ActRIIb protein or signaling mediated by activin. In certain embodiments, a functional variant of the ActRIIb polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated by modifying the structure of an ActRIIb polypeptide for such purposes as enhancing therapeutic efficacy, or stability (e.g., ex vivo shelf life and resistance to proteolytic degradation in vivo). Such modified ActRIIb polypeptides when selected to retain activin binding, are considered functional equivalents of the naturally-occurring ActRIIb polypeptides. Modified ActRIIb polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIb polypeptide results in a functional homolog can be readily determined by assessing the ability of the variant ActRIIb polypeptide to produce a response in cells in a fashion similar to the wild-type ActRIIb polypeptide.

In certain embodiments, the present invention contemplates specific mutations of the ActRIIb polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the wild-type ActRIIb polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIb polypeptide is by chemical or enzymatic coupling of glycosides to the ActRIIb polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on an ActRIIb polypeptide may be accomplished chemically and/or enzymatically. Chemical deglycosylation may involve, for example, exposure of the ActRIIb polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on ActRIIb polypeptides can be achieved by the use of a variety of endo- and exo-glycosidases as described by Thotakura et al. (1987) Meth. Enzymol. 138:350. The sequence of an ActRIIb polypeptide may be adjusted, as appropriate, depending on the type of expression system used, as mammalian, yeast, insect and plant cells may all introduce differing glycosylation patterns that can be affected by the amino acid sequence of the peptide. In general, ActRIIb proteins for use in humans may be expressed in a mammalian cell line that provides proper glycosylation, such as HEK293 or CHO cell lines, although other mammalian expression cell lines are expected to be useful as well. Other non-mammalian cell lines may be used (e.g., yeast, *E. coli*, insect cells), and in some cases, such cell lines may be engineered to include enzymes that confer mammalian-type glycosylation patterns on the expressed proteins.

This disclosure further contemplates a method of generating mutants, particularly sets of combinatorial mutants of an ActRIIb polypeptide, as well as truncation mutants; pools of combinatorial mutants are especially useful for identifying functional variant sequences. The purpose of screening such combinatorial libraries may be to generate, for example, ActRIIb polypeptide variants which bind to activin or other ligands. A variety of screening assays are provided below, and such assays may be used to evaluate variants. For example, an ActRIIb polypeptide variant may be screened for ability to bind to an ActRIIb ligand, to prevent binding of an ActRIIb ligand to an ActRIIb polypeptide or to interfere with signaling caused by an ActRIIb ligand.

The activity of an ActRIIb polypeptide or its variants may also be tested in a cell-based or in vivo assay. For example, the effect of an ActRIIb polypeptide variant on the expression of genes involved in hematopoiesis may be assessed. This may, as needed, be performed in the presence of one or more recombinant ActRIIb ligand proteins (e.g., activin), and cells may be transfected so as to produce an ActRIIb polypeptide and/or variants thereof, and optionally, an ActRIIb ligand. Likewise, an ActRIIb polypeptide may be administered to a mouse or other animal, and one or more blood measurements, such as an RBC count, hemoglobin, or reticulocyte count may be assessed.

Combinatorially-derived variants can be generated which have a selective or generally increased potency relative to a naturally occurring ActRIIb polypeptide. Likewise, mutagenesis can give rise to variants which have intracellular half-lives dramatically different than the corresponding a wild-type ActRIIb polypeptide. For example, the altered protein can be rendered either more stable or less stable to proteolytic degradation or other cellular processes which result in destruction of, or otherwise inactivation of a native ActRIIb polypeptide. Such variants, and the genes which encode them, can be utilized to alter ActRIIb polypeptide levels by modulating the half-life of the ActRIIb polypeptides. For instance, a short half-life can give rise to more transient biological effects and, when part of an inducible expression system, can allow tighter control of recombinant ActRIIb polypeptide levels within the cell. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIb polypeptide sequences. For instance, a mixture of synthetic oligonucleotides can be enzymatically ligated into gene sequences such that the degenerate set of potential ActRIIb polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIb polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIb polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIb polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, the ActRIIb polypeptides of the invention may further comprise post-translational modifications in addition to any that are naturally present in the ActRIIb polypeptides. Such modifications include, but are not limited to, acetylation, carboxylation, glycosylation, phosphorylation, lipidation, and acylation. As a result, the modified ActRIIb polypeptides may contain non-amino acid elements, such as polyethylene glycols, lipids, poly- or mono-saccharide, and phosphates. Effects of such non-amino acid elements on the functionality of an ActRIIb polypeptide may be tested as described herein for other ActRIIb polypeptide variants. When an ActRIIb polypeptide is produced in cells by cleaving a nascent form of the ActRIIb polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIb polypeptides.

In certain aspects, functional variants or modified forms of the ActRIIb polypeptides include fusion proteins having at least a portion of the ActRIIb polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) (SEQ ID NO: 23) fusion partners. As another example, a fusion domain may be selected so as to facilitate detection of the ActRIIb polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIb polypeptide is fused with a domain that stabilizes the ActRIIb polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Constant domains from an immunoglobulin, particularly an IgG heavy chain, may also be used as stabilizing domains. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

An example of an IgG1 Fc domain is shown below (SEQ ID NO: 7).

THTCPPCPAPELLGGPSVFLFPPKPKDTLMISRTPEVTCVVVD (A)

VSHEDPEVKFNWYVDGVEVHNAKTKPREEQYNSTYRVVSVLTVLHQ

DWLNGKEYKCK (A) VSNKALPVPIEKTISKAKGQPREPQVYTLP

PSREEMTKNQVSLTCLVKGFYPSDIAVEWESNGQPENNYKTTPPVL

DSDGPFFLYSKLTVDKSRWQQGNVFSCSVMHEALHN (A) HYTQK

SLSLSPGK*

As an additional specific example, the present invention provides a fusion protein comprising a soluble extracellular domain of ActRIIb fused to an Fc domain (Fc portion underlined) (e.g., SEQ ID NO: 6).

SGRGEAETRECIYYNANWELERTNQSGLERCEGEQDKRLHCYASWRNS

SGTIELVKKGCWLDDFNCYDRQECVATEENPQVYFCCCEGNFCNERFT

HLPEAGGPEVTYEPPPTAPTGGGTHTCPPCPAPELLGGPSVFLFPPKP

KDTLMISRTPEVTCVVVDVSHEDPEVKFNWYVDGVEVHNAKTKPREEQ

YNSTYRVVSVLTVLHQDWLNGKEYKCKVSNKALPVPIEKTISKAKGQP

REPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQK

SLSLSPGK

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain. Fc domains from IgG2, IgG3 and IgG4 may also be used.

It is understood that different elements of the fusion proteins may be arranged in any manner that is consistent with the desired functionality. For example, an ActRIIb polypeptide may be placed C-terminal to a heterologous domain, or, alternatively, a heterologous domain may be placed C-terminal to an ActRIIb polypeptide. The ActRIIb polypeptide domain and the heterologous domain need not be adjacent in a fusion protein, and additional domains or amino acid sequences may be included C- or N-terminal to either domain or between the domains.

In certain embodiments, the ActRIIb polypeptides of the present invention contain one or more modifications that are capable of stabilizing the ActRIIb polypeptides. For example, such modifications enhance the in vitro half life of the ActRIIb polypeptides, enhance circulatory half life of the ActRIIb polypeptides or reducing proteolytic degradation of the ActRIIb polypeptides. Such stabilizing modifications include, but are not limited to, fusion proteins (including, for example, fusion proteins comprising an ActRIIb polypeptide and a stabilizer domain), modifications of a glycosylation site (including, for example, addition of a glycosylation site to an ActRIIb polypeptide), and modifications of carbohydrate moiety (including, for example, removal of carbohydrate moieties from an ActRIIb polypeptide). As used herein, the term "stabilizer domain" not only refers to a fusion domain (e.g., Fc) as in the case of fusion proteins, but also includes nonproteinaceous modifications such as a carbohydrate moiety, or nonproteinaceous moiety, such as polyethylene glycol.

In certain embodiments, the present invention makes available isolated and/or purified forms of the ActRIIb polypeptides, which are isolated from, or otherwise substantially free of, other proteins. ActRIIb polypeptides will generally be produced by expression from recombinant nucleic acids.

3. Nucleic Acids Encoding ActRIIb Polypeptides

In certain aspects, the invention provides isolated and/or recombinant nucleic acids encoding any of the ActRIIb polypeptides (e.g., full-length and soluble ActRIIb polypeptides), including fragments, functional variants and fusion proteins disclosed herein. For example, SEQ ID NO: 4 encodes the naturally occurring human ActRIIb precursor polypeptide, while SEQ ID NO: 5 encodes the processed extracellular domain of ActRIIb. The subject nucleic acids may be single-stranded or double stranded. Such nucleic acids may be DNA or RNA molecules. These nucleic acids may be used, for example, in methods for making ActRIIb polypeptides or as direct therapeutic agents (e.g., in a gene therapy approach).

In certain aspects, the subject nucleic acids encoding ActRIIb polypeptides are further understood to include nucleic acids that are variants of SEQ ID NO: 4 or 5. Variant nucleotide sequences include sequences that differ by one or more nucleotide substitutions, additions or deletions, such as allelic variants.

In certain embodiments, the invention provides isolated or recombinant nucleic acid sequences that are at least 80%, 85%, 90%, 95%, 97%, 98%, 99% or 100% identical to SEQ ID NOs: 4, 5, or 10. One of ordinary skill in the art will appreciate that nucleic acid sequences complementary to SEQ ID NOs: 4, 5, or 10 and variants of SEQ ID NOs: 4, 5, or 10 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences, and the ActRIIb polypeptides encoded by such nucleic acids that hybridize under highly stringent conditions to the nucleotide sequence designated in SEQ ID NOs: 4, 5, or 10, the complement sequence of SEQ ID NOs: 4, 5, or 10, or fragments of any of the foregoing. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 4, 5, or 10 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIb polypeptide and operably linked to at least one regulatory sequence. Regulatory sequences are art-recognized and are selected to direct expression of the ActRIIb polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIb polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIb polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both pro-karyotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIb polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIb polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 4, 5, or 10) for one or more of the subject ActRIIb polypeptides. The host cell may be any prokaryotic or eukaryotic cell. For example, an ActRIIb polypeptide of the invention may be expressed in bacterial cells such as E. coli, insect cells (e.g., using a baculovirus expression system), yeast, or mammalian cells. Other suitable host cells are known to those skilled in the art.

Accordingly, the present invention further pertains to methods of producing the subject ActRIIb polypeptides. For example, a host cell transfected with an expression vector encoding an ActRIIb polypeptide can be cultured under appropriate conditions to allow expression of the ActRIIb polypeptide to occur. The ActRIIb polypeptide may be secreted and isolated from a mixture of cells and medium containing the ActRIIb polypeptide. Alternatively, the ActRIIb polypeptide may be retained cytoplasmically or in a membrane fraction and the cells harvested, lysed and the protein isolated. A cell culture includes host cells, media and other byproducts. Suitable media for cell culture are well known in the art. The subject ActRIIb polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIb polypeptides and affinity purification with an agent that binds to a domain fused to the ActRIIb polypeptide (e.g., a protein A column may be used to purify an ActRIIb-Fc fusion). In a preferred embodiment, the ActRIIb polypeptide is a fusion protein containing a domain which facilitates its purification. In a preferred embodiment, purification is achieved by a series of column chromatography steps, including, for example, three or more of the following, in any order: protein A chromatography, Q SEPHAROSE® (a cross-linked beaded form of agarose) chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant ActRIIb polypeptide, can allow purification of the expressed fusion protein by affinity chromatography using a $Ni^{2+}$ metal resin. The purification leader sequence can then be subsequently removed by treatment with enterokinase to provide the purified ActRIIb polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Alternative ActRIIb Antagonists

As demonstrated herein, an ActRIIb polypeptide is effective to increase reticulocyte levels in vivo, an effect which, over a longer time period leads to increased hematocrit levels in certain species, and is likely to do so in humans. Thus, in some embodiments, ActRIIb antagonists of the disclosure may be used increase red blood cell levels in vivo. Although soluble ActRIIb polypeptides, and particularly ActRIIb-Fc, are preferred antagonists, and although such antagonists may affect red blood cell levels through a mechanism other than activin antagonism (e.g., activin inhibition may be an indicator of the tendency of an agent to inhibit the activities of a spectrum of molecules, including, perhaps, other members of the TGF-beta superfamily, and such collective inhibition may lead to the desired effect on hematopoiesis), other types of ActRIIb antagonists are expected to be useful, including anti-ActRIIb antibodies, antisense, RNAi or ribozyme nucleic acids that inhibit the production of ActRIIb, and other inhibitors of ActRIIb, particularly those that disrupt ActRIIb binding.

An antibody that is specifically reactive with an ActRIIb polypeptide (e.g., a soluble ActRIIbpolypeptide) and which either binds competitively to ligand with the ActRIIb polypeptide or otherwise inhibits ActRIIb-mediated signaling may be used as an antagonist of ActRIIb polypeptide activities.

By using immunogens derived from an ActRIIb polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRIIb polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRIIb polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRIIb polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRIIb polypeptide and monoclonal antibodies isolated from a culture comprising such hybridoma cells.

The term "antibody" as used herein is intended to include whole antibodies, e.g., of any isotype (IgG, IgA, IgM, IgE, etc), and includes fragments or domains of immunoglobulins which are reactive with a selected antigen. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies. The term "recombinant antibody", means an antibody, or antigen binding domain of an immunoglobulin, expressed from a nucleic acid that has been constructed using the techniques of molecular biology, such as a humanized antibody or a fully human antibody developed from a single chain antibody. Single domain and single chain antibodies are also included within the term "recombinant antibody".

In certain embodiments, an antibody of the invention is a monoclonal antibody, and in certain embodiments, the invention makes available methods for generating novel antibodies. For example, a method for generating a monoclonal antibody that binds specifically to an ActRIIb polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRIIb polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ M or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are ActRIIb antagonists include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100, or no more than 50, 35, 25, 22, 20, 18 or 15 nucleotides of the full-length ActRIIb nucleic acid sequence. The region of complementarity will preferably be at least 8 nucleotides, and optionally about 18 to 35 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will generally have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, red blood cell levels.

In certain embodiments, alternative antagonists with properties that are similar to ActRIIb antagonists may be used. An antagonist may be a follistatin polypeptide that antagonizes activin bioactivity and/or binds to activin and/or myostatin. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 18-20, the N-terminus follistatin domain ("FSND" SEQ ID NO: 18), FSD2 (SEQ ID NO: 19), and to a lesser extent FSD1 (SEQ ID NO: 20) represent exemplary domains within follistatin important for activin binding. In addition, methods for making and testing libraries of polypeptides are described above in the context of ActRIIb polypeptides and such methods also pertain to making and testing variants of follistatin. Additionally, forms of follistatin that bind myostatin preferentially (with reduced activin binding) are also known and may be used as antagonists herein that may exhibit properties similar to those of ActRIIb antagonists;

such follistatin forms may be found in, for example, WO/2005/100563 and WO/2008/030367). Follistatin polypeptides include polypeptides derived from the sequence of any known follistatin having a sequence at least about 80% identical to the sequence of a follistatin polypeptide, and optionally at least 85%, 90%, 95%, 97%, 99% or greater identity. Examples of follistatin polypeptides include the mature follistatin polypeptide or shorter isoforms or other variants of the human follistatin precursor polypeptide (SEQ ID NO: 16) as described, for example, in WO2005/025601.

The human follistatin precursor polypeptide isoform FST344 is as follows:

MVRARHQPGGLCLLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHGSCNSISEDTEEEEEDEDQDYSFPISSILEW(SEQ ID

NO: 16; NP_037541.1 FOLLISTATIN ISOFORM FST344)

The signal peptide is single underlined; the last 27 residues in bold represent additional amino acids as compared to a shorter follistatin isoform FST317 (NP 006341) below.

The human follistatin precursor polypeptide isoform FST317 is as follows:

(SEQ ID NO: 17)
MVRARHQPGGLCLLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECAMKEA

ACSSGVLLEVKHSGSCN

The signal peptide is single underlined.

N-terminus follistatin domain (FSND) sequence is as follows:

(SEQ ID NO: 18; FSND)
GNCWLRQAKNGRCQVLYKTELSKEECCSTGRLSTSWTEEDVNDNTLFKW

MIFNGGAPNCIPCK

The FSD1 and FSD2 sequences are as follows:

(SEQ ID NO: 19; FSD1)
ETCENVDCGPGKKCRMNKKNKPRCV (SEQ ID NO: 20; FSD2)
KTCRDVFCPGSSTCVVDQTNNAYCVT

In other embodiments, an antagonist similar to an ActRIIb antagonist may be a follistatin-like related gene (FLRG) that antagonizes activin bioactivity and/or binds to activin. The term "FLRG polypeptide" includes polypeptides comprising any naturally occurring polypeptide of FLRG as well as any variants thereof (including mutants, fragments, fusions, and peptidomimetic forms) that retain a useful activity. Variants of FLRG polypeptides that retain activin or myostatin binding properties can be identified using routine methods to assay FLRG and activin or myostatin interactions. See, for example, U.S. Pat. No. 6,537,966. In addition, methods for making and testing libraries of polypeptides are described above in the context of ActRIIb polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor polypeptide is as follows:

(SEQ ID NO: 21;NP_005851)
MRPGAPGPLWPLPWGALAWAVGFVSSMGSGNPAPGGVCWLQQGQEATCSL

VLQTDVTRAECCASGNIDTAWSNLTHPGNKINLLGFLGLVHCLPCKDSCD

GVECGPGKACRMLGGRPRCECAPDCSGLPARLQVCGSDGATYRDECELRA

ARCRGHPDLSVMYRGRCRKSCEHVVCPRPQSCVVDQTGSAHCVVCRAAPC

VPSSPGQELCGNNNVTYISSCHMRQATCFLGRSIGVRHAGSCAGTPEEPP

GGESAEEEENFV

The signal peptide is single underlined.

In certain embodiments, functional variants or modified forms of the follistatin polypeptides and FLRG polypeptides include fusion protein having at least a portion of the follistatin polypeptides or FLRG polypeptides and one or more fusion domains, such as, for example, domains that facilitate isolation, detection, stabilization or multimerization of the polypeptide. Suitable fusion domains are discussed in detail above with reference to the ActRIIb polypeptides. In one embodiment, an antagonist is a fusion protein comprising a ligand binding (e.g. activin binding) portion of a follistaton polypeptide fused to an Fc domain. In another embodiment, an antagonist is a fusion protein comprising a ligand binding (e.g. activin binding) portion of an FLRG polypeptide fused to an Fc domain. Follistatin and FLRG have been shown in the literature, and by the applicants with respect to FLRG, to have affinities for Activin A in the picomolar range, indicating that these agents will inhibit activin A signaling to a similar degree as ActRIIb-Fc.

5. Exemplary Therapeutic Methods

In certain embodiments, the present invention provides methods for managing a patient that has been treated with, or is a candidate to be treated with, an ActRIIb antagonist or other antagonist described herein by measuring one or more hematologic parameters in the patient. The hematologic parameters may be used to evaluate appropriate dosing for a patient who is a candidate to be treated with an ActRIIb anatagonist or other antagonist described herein, to monitor the hematologic parameters during treatment with an ActRIIb antagonist, to evaluate whether to adjust the dosage during treatment with an ActRIIb antagonist, and/or to evaluate an appropriate maintenance dose of an ActRIIb antagonist. If one or more of the hematologic parameters are outside the normal level, dosing with the ActRIIb antagonist may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

Red blood cell levels may be determined, for example, by determining a red blood cell count, by measuring hemoglobin levels or by measuring hematocrit levels. A red blood cell count may be determined using a commercially available Coulter Counter. The normal range for a red blood cell count is between 4.2-5.9 million cells/cm, although individual variations should be taken into account. Hemoglobin levels may be determined by lysing the red blood cells, converting the hemoglobin into cyanomethemoglobin and measuring the amount of hemoglobin with a colorimeter. The normal ranges for hemoglobin are 14-18 gm/dl for adult males and 12-16 gm-dl for adult females, although individual variations should be taken into account. Hematocrit (Hct) or packed cell volume (PCV) refers to the ratio of the volume of red blood cells to the volume of whole blood. Hematocrit may be determined, for example, by centrifugation of a blood sample followed by analysis of the layers produced. Normal ranges for hematocrit are approximately 41-51% for men and 35-45% for women, although individual variations should be taken into account.

Blood pressure, including systolic blood pressure, diastolic blood pressure, or mean arterial blood pressure, may be determined using art recognized methods. Blood pressure is most commonly measured using a sphygmomanometer. Typical values for a resting, healthy adult human are approximately 120 mmHg systolic and 80 mmHg diastolic, although individual variations should be taken into account. Individuals suffering from hypertension typically have a blood pressure ≥140 mmHg systolic and ≥90 diastolic blood pressure. Individuals having a level above normal but less than 140/90 mmHg are generally referred to as prehypertensive. Additional methods for measuring blood pressure may be found in Pickering et al., Hypertension 45: 142-161 (2005).

Iron stores may be measured using a variety of art recognized techniques including, for example, by determining levels of one or more of the following: serum ferritin (SF), transferrin saturation (TSAT), total iron binding capacity, hemoglobin concentration, zinc protoporphyrin, mean cell volume (MCV), or transferrin receptor in serum. Serum ferritin levels may be determined, for example, using an immunoassay such as an enzyme-linked immunosorbent assay (ELISA) or immunoturbidometry. In normal patients, serum ferritin levels range from 13 to 220 ng/mL, although individual variations should be taken into account. Transferrin saturation levels represent the proportion of transferrin bound to iron and may be determined by dividing serum iron by total iron biding capacity (TIBC). In normal patients, transferrin saturation levels range from 20% to 40%, although individual variations should be taken into account. Serum iron may be determined using colorimetry and is expressed as ug/dl or umol/l. Total iron binding capacity reflects the total capacity of circulating transferrin bound to iron and may be determined using a colorimetric assay to determine the amount of iron that can be bound to unsaturated transferrin in vitro. The normal range of total iron binding capacity is about 250-450 ug/dl, although individual variations should be taken into account. Additional information about measuring iron stores may be found in the World Health Organization report entitled Assessing the Iron Status of Populations dated April 2004 and in Yamanishi et al., Clinical Chemistry 48: 1565-1570 (2002).

In one embodiment, if one or more hematologic parameters are outside the normal range, or on the high side of normal, in a patient who is a candidate to be treated with an ActRIIb antagonist then onset of administration of the ActRIIb antagonist may be delayed until the hematologic parameters have returned to a normal or acceptable level either naturally or via therapeutic intervention. For example, if a candidate patient is hypertensive or prehypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the ActRIIb antagonist may be delayed until the levels have returned to a normal or acceptable level.

In certain embodiments, if one or more hematologic parameters are outside the normal range, or on the high side of normal, in a patient who is a candidate to be treated with an ActRIIb antagonist then the onset of administration may be not be delayed. However, the dosage amount or frequency of dosing of the ActRIIb antagonist may be set at an amount that would reduce the risk of an unacceptable increase in the hematologic parameters arising upon administration of the ActRIIb antagonist. Alternatively, a therapeutic regimen may be developed for the patient that combines an ActRIIb antagonist with a therapeutic agent that addresses the undesirable level of the hematologic parameter. For example, if the patient has elevated blood pressure, then a therapeutic regimen involving administration of an ActRIIb antagonist and a blood pressure lowering agent may be designed. For a patient having lower than desired iron stores, a therapeutic regimen of an ActRIIb antagonist and iron supplementation may be developed.

In one embodiment, baseline parameter(s) for one or more hematologic parameters may be established for a patient who is a candidate to be treated with an ActRIIb antagonist and an appropriate dosing regimen establish for that patient based on the baseline value(s). Alternatively, established baseline parameters based on a patient's medical history could be used to inform an appropriate ActRIIb antagonist dosing regimen for a patient. For example, if a healthy patient has an established baseline blood pressure reading that is above the defined normal range it may not be necessary to bring the patient's blood pressure into the range that is considered normal for the general population prior to treatment with the ActRIIb antagonist. A patient's baseline values for one or more hematologic parameters prior to treatment with an ActRIIb antagonist may also be used as the relevant comparative values for monitoring any changes to the hematologic parameters during treatment with the ActRIIb antagonist.

In certain embodiments, one or more hematologic parameters are measured in patients who are being treated with an ActRIIb antagonist. The hematologic parameters may be used to monitor the patient during treatment and permit adjustment or termination of the dosing with the ActRIIb antagonist or additional dosing with another therapeutic agent. For example, if administration of an ActRIIb antagonist results in an increase in blood pressure, red blood cell level, or hemoglobin level, or a reduction in iron stores, then the dose of the ActRIIb antagonists may be reduced in amount or frequency in order to decrease the effects of the ActRIIb antagonist on the one or more hematologic parameters. If administration or an ActRIIb antagonist results in a change in one or more hematologic parameters that is adverse to the patient, then the dosing of the ActRIIb antagonist may be terminated either temporarily, until the hematologic parameter(s) return to an acceptable level, or permanently. Similarly, if one or more hematologic parameters are not brought within an acceptable range after reducing the dose or frequency of administration of the ActRIIb antagonist then the dosing may be terminated. As an alternative, or in addition to, reducing or terminating the dosing with the ActRIIb antagonist, the patient may be dosed with an additional therapeutic agent that addresses the undesirable level in the hematologic parameter(s), such as, for example, a blood pressure lowering agent or an iron supplement. For example, if a patient being treated with an ActRIIb antagonist has elevated blood pressure, then dosing with the ActRIIb antagonist may continue at the same level and a blood pressure lowering agent is added to the treatment regimen, dosing with the ActRIIb antagonist may be reduce (e.g., in amount and/or frequency) and a blood pressure lowering agent is added to the treatment regimen, or dosing with the ActRIIb antagonist may be terminated and the patient may be treated with a blood pressure lowering agent.

In certain embodiments, if a patient being treated with an ActRIIb antagonist or a patient who is a candidate for treatment with an ActRIIb antagonist has one or more of the following: a hemoglobin level greater than 12 g/dl, a hemoglobin level greater than 15 g/dl, a blood pressure≥120/80 mmHg, a blood pressure≥140/90 mmHg, a transferrin saturation level less than 20%, and/or a ferritin level less than 100 ng/ml, then dosing with the ActRIIb antagonist is reduced, delayed or terminated. As an alternative, or in addition to, reducing, delaying or terminating dosing with ActRIIb antagonist, a therapeutic agent that addresses the undesired level of one or more hematologic parameters (such as a blood pressure lowering agent or an iron supplement) may be administered to the patient.

In one embodiment, the present invention provides a method for dosing a patient with an ActRIIb antagonist by administering to the patient an ActRIIb antagonist in an amount and at a frequency which reduces the risk of causing a rise in hemoglobin levels greater than 1 g/dl over a two week period. The methods may comprise measuring one or more hematologic parameters either before beginning administration of the ActRIIb antagonist and/or during administration of the ActRIIb antagonist. The initial dose of the ActRIIb antagonist may be set so as to reduce the risk of causing a rise in hemoglobin levels greater than 1 g/dl over a two week period. In addition, the dose may be adjusted over time to in order to maintain a reduced risk of causing a rise in hemoglobin levels greater than 1 g/dl in two weeks.

In certain embodiments, the present invention provides a method for administering an ActRIIb-Fc fusion protein to a patient by administering the ActRIIb fusion protein no more frequently than once per 10 days, once per 20 days, once per 30 days, once per 45 days, once per 60 days, once per 90 days, or once per 120 days, or 1-6 times per year, 2-6 times per year, 1-5 times per year, 2-5 times per year, 1-4 times per year, 2-4 times per year, 1-3 times per year, or 2-3 times per year.

In certain embodiments, the invention provides methods for determining dosing and monitoring therapeutic progress with ActRIIb antagonist treatment in patients in which the ActRIIb antagonist is being administered to increase red blood cell levels. The methods involve determining one or more hematologic parameters either prior to beginning dosing with the ActRIIb antagonist and/or during treatment with the ActRIIb antagonist. For example, one or more hematologic parameters may be determined in a patient who is a candidate for administration of an ActRIIb antagonist for increasing blood cell levels to facilitate determination of dosage amount and frequency. One or more hematologic parameters may also be determined in a patient being treated with an ActRIIb antagonist for purposes of increasing red blood cell levels in order to monitor progress of the treatment, facilitate dosing adjustments, and to determine maintenance dosing levels, etc.

In accordance with the methods of the invention, one or more hematologic parameters may be measured at various time points and at varying frequencies as needed for an individual patient based on various factors such as a patient's baseline levels, responsiveness to treatment with an ActRIIb antagonist, general health, age, sex, weight, etc. Measuring of one or more hematologic parameters may be carried out before and/or during treatment with an ActRIIb antagonist. If conducting multiple measurements of hematologic parameters at various time points, the same set of hematologic parameter(s) need not be measured at each time point. Similarly, the same test for an individual parameter need not be used at each time point. Appropriate hematologic parameters and tests for such parameters may be chosen for an individual taking into account factors specific to the given individual. Testing of hematologic parameters may occur as frequently as needed for a given individual, such as, for example, once per day, once per week, once per every two weeks, once per month, once per each 2 month period, once per each 3 month period, once per each 6 month period, or once per year. In addition, the frequency of testing may vary over time. For example, upon initial dosing of an individual it may be desirable to test for one or more hematologic parameters more frequently, e.g., once per day, once per week, once per every two weeks, or once per month, and then decrease the frequency of testing over time, e.g., after one month, two months, six months, 1 year, two years, or longer, of treatment, the frequency of testing may reduced to, for example, once per month, once per every two months, once per every three months, once per every six months, or once per year. Similarly, it may be desirable to test more frequently when adjusting a patient's dose of an ActRIIb antagonist (e.g., either amount or frequency of administration) and then decrease the frequency of testing over time, for example, once the patient's response to the ActRIIb antagonist has been established.

In various embodiments, patients being treated with an ActRIIb antagonist, or candidate patients for treatment with an ActRIIb antagonist, may be mammals such as rodents and primates, and particularly human patients.

In certain embodiments, patients being treated with an ActRIIb antagonist, or candidate patients to be treated with an ActRIIb antagonist, are patients in need of bone and/or cartilage formation, prevention of bone loss, increased bone mineralization or prevention of bone demineralization, such as patients with low bone density, decreased bone strength, or bone damage due to breakage, loss or demineralization. In exemplary embodiments, the patients or candidate patients may be patients suffering from, or at risk for developing, osteoporosis (including secondary osteoporosis), hyperparathyroidism, Cushing's disease, Paget's disease, thyrotoxicosis, chronic diarrheal state or malabsorption, renal tubular acidosis, or anorexia nervosa. Osteoporosis resulting from drugs or another medical condition is known as secondary osteoporosis. Medications that can cause secondary osteoporosis include, for example, corticosteroids, methotrexate (Rheumatrex, Immunex, Folex PFS), cyclosporine (Sandimmune, Neoral), luteinizing hormone-releasing hormone agonists (Lupron, Zoladex), and heparin (Calciparine, Liquaemin). Bone loss resulting from cancer therapy is widely recognized and termed cancer therapy induced bone loss (CTIBL).

In certain embodiments, patients being treated with an ActRIIb antagonist, or candidate patients to be treated with an ActRIIb antagonist, are patients in need of muscle growth, such as patients suffering from, or at risk of developing, a neuromuscular disorder or musculogenerative disorder. For example, patients or candidate patients may be suffering from, or at risk for developing, Lou Gehrig's disease (ALS), cancer anorexia-cachexia syndrome, muscular dystrophy, muscle atrophy, congestive obstructive pulmonary disease (and muscle wasting associated with COPD), muscle wasting syndrome, sarcopenia, or cachexia. Muscular dystrophy refers to a group of degenerative muscle diseases characterized by gradual weakening and deterioration of skeletal muscles and sometimes the heart and respiratory muscles. Exemplary muscular dystrophies that can be treated with a regimen including the subject ActRIIB polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), Congenital Muscular Dystrophy (CMD).

In certain embodiments, patients being treated with an ActRIIb antagonist, or candidate patients to be treated with an ActRIIb antagonist, are patients with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss, such as having blood drawn and stored for a later transfusion. Patients and candidate patients may also include those patients in need of an increase in red blood cells and/or hemoglobin levels that do not respond well to Epo. When observing hemoglobin levels in humans, a level of less than normal for the appropriate age and gender category may be indicative of anemia, although individual variations are taken into account. Potential causes of anemia include blood-loss, nutritional deficits, medication reaction, various problems with the bone marrow and many diseases. More particularly, anemia has been associated with a variety of disorders that include, for example, chronic renal failure, myelodysplastic syndrome, rheumatoid arthritis, bone marrow transplantation. Anemia may also be associated with the following conditions: solid tumors (e.g. breast cancer, lung cancer, colon cancer); tumors of the lymphatic system (e.g. chronic lymphocyte leukemia, non-Hodgkins and Hodgkins lymphomas); tumors of the hematopoietic system (eg. leukemia, myelodysplastic syndrome, multiple myeloma);

radiation therapy; chemotherapy (e.g. platinum containing regimens); inflammatory and autoimmune diseases, including, but not limited to, rheumatoid arthritis, other inflammatory arthritides, systemic lupus erythematosis (SLE), acute or chronic skin diseases (e.g. psoriasis), inflammatory bowel disease (e.g. Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g. some Jehovah's Witnesses); infections (e.g. malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician or other health care provider and the intended result of administration of the therapeutic agent.

6. Pharmaceutical Compositions

In certain embodiments, ActRIIb antagonists (e.g., ActRIIb polypeptides) of the present invention are formulated with a pharmaceutically acceptable carrier. For example, an ActRIIb polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally as an implant or device. When administered, the therapeutic composition for use in this invention is, of course, in a pyrogen-free, physiologically acceptable form. Therapeutically useful agents other than the ActRIIb antagonists which may also optionally be included in the composition as described above, may be administered simultaneously or sequentially with the subject compounds (e.g., ActRIIb polypeptides) in the methods of the invention.

Typically, ActRIIb antagonists will be administered parenterally. Pharmaceutical compositions suitable for parenteral administration may comprise one or more ActRIIb-polypeptides in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone marrow). In certain embodiments, compositions of the present invention may include a matrix capable of delivering one or more compounds (e.g., ActRIIb polypeptides) to a target tissue site (e.g., bone marrow), providing a structure for the developing tissue and optimally capable of being resorbed into the body. For example, the matrix may provide slow release of the ActRIIb polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject of the invention (e.g., ActRIIb polypeptides). The various factors include, but are not limited to, the patient's red blood cell count, hemoglobin level or other diagnostic assessments, the desired target red blood cell count, the patient's age, sex, and diet, the severity of any disease that may be contributing to a depressed red blood cell level, time of administration, and other clinical factors. The addition of other known growth factors to the final composition may also affect the dosage. Progress can be monitored by periodic assessment of red blood cell and hemoglobin levels, as well as assessments of reticulocyte levels and other indicators of the hematopoietic process.

In certain embodiments, effects on red blood cell levels in humans may be obtained when ActRIIb-Fc is dosed at intervals and amounts sufficient to achieve serum concentrations of about 100 ng/ml or greater, for a period of at least about 20 to 30 days. Dosing to obtain serum levels of 200 ng/ml, 500 ng/ml, 1000 ng/ml or greater for a period of at least 20 to 30 days may also be used. Bone effects can be observed at serum levels of about 200 ng/ml, with substantial effects beginning at about 1000 ng/ml or higher, over a period of at least about 20 to 30 days. Thus, if it is desirable to achieve effects on red blood cells while having little effect on bone, a dosing scheme may be designed to deliver a serum concentration of between about 100 and 1000 ng/ml over a period of about 20 to 30 days. Alternatively, if it is desirable to achieve effects on bone, muscle, etc., while having little effect on, or reducing effects on red blood cell levels, a dosing scheme may be designed to deliver a dosing scheme of between about 100 and 1000 ng/ml with a dosing frequency that occurs less than once every 60 days, once every 90 days, or once every 120 days. In humans, serum levels of 200 ng/ml may be achieved with a single dose of 0.1 mg/kg or greater and serum levels of 1000 ng/ml may be achieved with a single dose of 0.3 mg/kg or greater. The observed serum half-life of the molecule is between about 20 and 30 days, substantially longer than most Fc fusion proteins, and thus a sustained effective serum level may be achieved, for example, by dosing with about 0.05 to 0.5 mg/kg on a weekly or biweekly basis, or higher doses may be used with longer intervals between dosings. For example, doses of 0.1 to 1 mg/kg might be used on a monthly or bimonthly basis.

In certain embodiments, the present invention also provides gene therapy for the in vivo production of ActRIIb polypeptides. Such therapy would achieve its therapeutic effect by introduction of the ActRIIb polynucleotide sequences into cells or tissues having the disorders as listed above. Delivery of ActRIIb polynucleotide sequences can be achieved using a recombinant expression vector such as a chimeric virus or a colloidal dispersion system. Preferred for therapeutic delivery of ActRIIb polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIb polynucleotide.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIb polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of ActRIIb-Fc Fusion Proteins

Applicants constructed a soluble ActRIIb fusion protein that has the extracellular domain of human ActRIIb fused to a human or mouse Fc domain with a minimal linker (three glycine amino acids) in between. The constructs are referred to as ActRIIb-hFc and ActRIIb-mFc, respectively.

ActRIIb-hFc is shown below as purified from CHO cell lines (SEQ ID NO: 8):

GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT<u>GGGTHTCPPCPAPELLGGPSVFLFPPKPKDTLMIS</u>

<u>RTPEVTCVVVDVSHEDPEVKFNWYVDGVEVHNAKTKPREEQYNSTYRVVS</u>

<u>VLTVLHQDWLNGKEYKCKVSNKALPVPIEKTISKAKGQPREPQVYTLPPS</u>

<u>REEMTKNQVSLTCLVKGFYPSDIAVEWESNGQPENNYKTTPPVLDSDGSF</u>

<u>FLYSKLTVDKSRWQQGNVFSCSVMHEALHNHYTQKSLSLSPGK</u>

The ActRIIb-hFc and ActRIIb-mFc proteins were expressed in CHO cell lines. Three different leader sequences were considered:
(i) Honey bee mellitin (HBML): MKFLVNVALVFMVVYI-SYIYA (SEQ ID NO: 11);
(ii) Tissue Plasminogen Activator (TPA): MDAMKRGLC-CVLLLCGAVFVSP (SEQ ID NO: 12); and
(iii) Native: MGAAAKLAFAVFLISCSSGA (SEQ ID NO: 13).

The selected form employs the TPA leader and has the following unprocessed amino acid sequence (SEQ ID NO: 9):

MDAMKRGLCCVLLLCGAVFVSPGASGRGEAETRECIYYNANWELERTNQ

SGLERCEGEQDKRLHCYASWRNSSGTIELVKKGCWLDDFNCYDRQECVA

TEENPQVYFCCCEGNFCNERFTHLPEAGGPEVTYEPPPTAPT<u>GGGTHTC</u>

<u>PPCPAPELLGGPSVFLFPPKPKDTLMISRTPEVTCVVVDVSHEDPEVIU</u>

<u>NWYVDGVEVHNAKTKPREEQYNSTYRVVSVLTVLHQDWLNGKEYKCKVS</u>

<u>NKALPVPIEKTISKAKGQPREPQVYTLPPSREEMTKNQVSLTCLVKGFY</u>

<u>PSDIAVEWESNGQPENNYKTTPPVLDSDGSFFLYSKLTVDKSRWQQGNV</u>

<u>FSCSVMHEALHNHYTQKSLSLSPGK</u>

This polypeptide is encoded by the following nucleic acid sequence (SEQ ID NO: 10):

```
A TGGATGCAAT GAAGAGAGGG CTCTGCTGTG TGCTGCTGCT
  GTGTGGAGCA GTCTTCGTTT CGCCCGGCGC CTCTGGGCGT
  GGGGAGGCTG AGACACGGGA GTGCATCTAC TACAACGCCA
  ACTGGGAGCT GGAGCGCACC AACCAGAGCG GCCTGGAGCG
  CTGCGAAGGC GAGCAGGACA AGCGGCTGCA CTGCTACGCC
  TCCTGGCGCA ACAGCTCTGG CACCATCGAG CTCGTGAAGA
  AGGGCTGCTG GCTAGATGAC TTCAACTGCT ACGATAGGCA
  GGAGTGTGTG GCCACTGAGG AGAACCCCCA GGTGTACTTC
  TGCTGCTGTG AAGGCAACTT CTGCAACGAG CGCTTCACTC
  ATTTGCCAGA GGCTGGGGGC CCGGAAGTCA CGTACGAGCC
  ACCCCCGACA GCCCCCACCG GTGGTGGAAC TCACACATGC
  CCACCGTGCC CAGCACCTGA ACTCCTGGGG GGACCGTCAG
  TCTTCCTCTT CCCCCCAAAA CCCAAGGACA CCCTCATGAT
  CTCCCGGACC CCTGAGGTCA CATGCGTGGT GGTGGACGTG
  AGCCACGAAG ACCCTGAGGT CAAGTTCAAC TGGTACGTGG
  ACGGCGTGGA GGTGCATAAT GCCAAGACAA AGCCGCGGGA
  GGAGCAGTAC AACAGCACGT ACCGTGTGGT CAGCGTCCTC
  ACCGTCCTGC ACCAGGACTG GCTGAATGGC AAGGAGTACA
  AGTGCAAGGT CTCCAACAAA GCCCTCCCAG TCCCCATCGA
  GAAAACCATC TCCAAAGCCA AAGGGCAGCC CCGAGAACCA
  CAGGTGTACA CCCTGCCCCC ATCCCGGGAG GAGATGACCA
  AGAACCAGGT CAGCCTGACC TGCCTGGTCA AAGGCTTCTA
  TCCCAGCGAC ATCGCCGTGG AGTGGGAGAG CAATGGGCAG
  CCGGAGAACA ACTACAAGAC CACGCCTCCC GTGCTGGACT
  CCGACGGCTC CTTCTTCCTC TATAGCAAGC TCACCGTGGA
  CAAGAGCAGG TGGCAGCAGG GGAACGTCTT CTCATGCTCC
  GTGATGCATG AGGCTCTGCA CAACCACTAC ACGCAGAAGA
  GCCTCTCCCT GTCTCCGGGT AAATGA
```

N-terminal sequencing of the CHO-cell produced material revealed a major sequence of -GRGEAE (SEQ ID NO: 22). Notably, other constructs reported in the literature begin with an -SGR . . . sequence.

Purification could be achieved by a series of column chromatography steps, including, for example, three or more of the following, in any order: protein A chromatography, Q SEPHAROSE® (a cross-linked beaded form of agarose) chromatography, phenylsepharose chromatography, size exclusion chromatography, and cation exchange chromatography. The purification could be completed with viral filtration and buffer exchange.

ActRIIb-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Applicants generated a series of mutations in the extracellular domain of ActRIIB and produced these mutant proteins as soluble fusion proteins between extracellular ActRIIB and an Fc domain. The background ActRIIB-Fc fusion has the sequence of SEQ ID NO: 6. Various mutations, including N- and C-terminal truncations, were introduced into the background ActRIIB-Fc protein. Based on the data presented in Example 1, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into *E. coli* DH5 alpha, colonies were picked and DNAs were isolated. For murine constructs (mFc), a murine IgG2a was substituted for the human IgG1. All mutants were sequence verified.

All of the mutants were produced in HEK293T cells by transient transfection. In summary, in a 500 ml spinner, HEK293T cells were set up at $6 \times 10^5$ cells/ml in FREE-STYLE™ (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, protein A column and eluted with low pH (3.0) glycine buffer. After neutralization, these were dialyzed against PBS.

Mutants were also produced in CHO cells by similar methodology.

Mutants were tested in binding assays and/or bioassays described. Characteristics of various ActRIIb variants are described in WO/2008/097541 and WO/2006/012627, incorporated by reference herein. In some instances, assays were performed with conditioned medium rather than purified proteins. Additional variations of ActRIIb are described in U.S. application Ser. No. 12/012,652.

Example 2. ActRIIb-hFc Stimulates Erythropoiesis in Non-Human Primates

ActRIIb-hFc (IgG1) was administered once a week for 1-month to male and female cynomolgus monkeys by subcutaneous injection. Forty-eight cynomolgus monkeys (24/sex) were assigned to one of four treatment groups (6 animals/sex/group) and were administered subcutaneous injections of either vehicle or ActRIIb-hFc at 3, 10, or 30 mg/kg once weekly for 4 weeks (total of 5 doses). Parameters evaluated included general clinical pathology (hematology, clinical chemistry, coagulation, and urinalysis). ActRIIb-hFc caused statistically significant elevated mean absolute reticulocyte values by day 15 in treated animals. By day 36, ActRIIb-hFc caused several hematological changes, including elevated mean absolute reticulocyte and red blood cell distribution width values and lower mean corpuscular hemoglobin concentration. All treated groups and both sexes were affected. These effects are consistent with a positive effect of ActRIIb-hFc on the release of immature reticulocytes from the bone marrow. This effect was reversed after drug was washed out of the treated animals (by study day 56). Accordingly, we conclude that ActRIIb-hFc stimulates erythropoiesis.

Example 3. ActRIIb-mFc Promotes Aspects of Erythropoiesis in Mice by Stimulation of Splenic Erythropoietic Activities In this study the effects of the in vivo administration of ActRIIb-mFc on the frequency of hematopoietic progenitors in bone marrow and spleen was analyzed. One group of Black6 mice was injected with PBS as a control and a second group of mice administered two doses of ActRIIb-mFc at 10 mg/kg and both groups sacrificed after 8 days. Peripheral blood was used to perform complete blood counts and femurs and spleens were used to perform in vitro clonogenic assays to assess the lymphoid, erythroid and myeloid progenitor cell content in each organ. In the brief time frame of this study, no significant changes were seen in red blood cell, hemoglobin or white blood cell levels in treated mice. In the femurs there was no difference in the nucleated cell numbers or progenitor content between the control and treated groups. In the spleens, the compound treated group experienced a statistically significant increase in the mature erythroid progenitor (CFU-E) colony number per dish, frequency and total progenitor number per spleen. In addition, and increase was seen in the number of myeloid (CFU-GM), immature erythroid (BFU-E) and total progenitor number per spleen.

Except for the strain of mouse used, the detailed methodology in this study was the same as that described above in Example 6. Mean values (+/−SD) for each group are shown in the tables below.

TABLE

| | Hematologic Parameters | | | |
|---|---|---|---|---|
| Treatment Group | White Blood Cells ($\times 10^9$/L) | Red Blood Cells ($\times 10^9$/L) | Hemoglobin (g/L) | Hematocrit (L/L) |
| PBS (n = 8) | 9.53 +/− 1.44 | 10.5 +/− 1.1 | 160.9 +/− 13.3 | 0.552 +/− 0.057 |
| ActRIIb-mFc (n = 8) | 9.77 +/− 1.19 | 10.8 +/− 0.3 | 162.1 +/− 4.1 | 0.567 +/− 0.019 |

TABLE

| Treatment Group | Total CFC per Femur | Total CFC per Spleen | Total CFU-E per Femur | Total CFU-E per Spleen |
|---|---|---|---|---|
| PBS (n = 8) | 88 +/− 10 | 54 +/− 14 | 156 +/− 27 | 131 +/− 71 |
| ActRIIb-mFc (n = 8) | 85 +/− 9 | 79 +/− 6* | 164 +/− 23 | 436 +/− 86* |

*preliminary analysis indicates $p < 0.05$

Treatment of mice with ActRIIb-mFc, in the brief time frame of this study, did not result in significant increases in red blood cell or hemoglobin content. In the femurs there was no difference in the nucleated cell numbers or progenitor content between the control and treated groups. In the spleens, the compound treated group experienced a statistically significant increase in the nucleated cell number before red blood cell lysis and in the mature erythroid progenitor (CFU-E) colony number per dish, frequency and total progenitor number per spleen. In addition, an increase was seen in the number of myeloid (CFU-GM), immature erythroid (BFU-E) and total progenitor number per spleen. Accordingly, it is expected that over a longer time course, ActRIIb-mFc treatment may result in elevated red blood cell and hemoglobin content.

Example 4. Effects of ActRIIb-Fc on Various Species in Longer-Term Studies

ActRIIb-Fc has a statistically significant effect on hematologic parameters in rodents. In a 3-month multidose study of ActRIIb-hFc in rats, significant increases in hemoglobin concentration or RBC count were observed, and reticulocyte concentrations increased in a dose-dependent manner.

TABLE

Hematologic parameters in 3-month study in Sprague-Dawley rats

| Sex (n) | Males (10/group) | | | |
|---|---|---|---|---|
| Dose (mg/kg) | Vehicle | 3 | 10 | 60 |
| RBC ($\times 10^6/\mu L$) | 8.6 | 9.9* | 10.2* | 9.1* |
| Hemoglobin (g/dL) | 15.9 | 17.4* | 17.9* | 16.4 |
| Reticulocytes ($\times 10^9/L$) | 176 | 250* | 272* | 446* |
| Sex (n) | Females (10/group) | | | |
| Dose (mg/kg) | Vehicle | 3 | 10 | 30 |
| RBC ($\times 10^6/\mu L$) | 8.2 | 8.7 | 9.3* | 9.7* |
| Hemoglobin (g/dL) | 15.7 | 16.2 | 16.5 | 17.5 |
| Reticulocytes ($\times 10^9/L$) | 169 | 200 | 239 | 332* |

*Statistically significant vs. vehicle ($P \leq 0.05$)

Interestingly, in a 3-month multidose study of ActRIIB-hFc in cynomolgus monkeys there were no significant increases in hematocrit levels, hemoglobin levels, or RBC count, and reticulocyte concentrations increased modestly over the course of the study. In a Phase Ia trial of ActRIIB-hFC, there were increases in hematologic parameters at some doses, with elevations typically observed at the highest dose levels within days of the first dose and at study completion. These data indicate that ActRIIB-Fc fusion proteins can be used to increase hematologic parameters in humans.

Example 5. ActRIIb-mFc Increases Muscle Mass in Mice

As described in U.S. patent application Ser. No. 12/012,652, ActRIIb-mFc is effective to promote growth of muscle mass in a variety of mouse models of human muscle disorders, including muscle dystrophy, amyotrophic lateral sclerosis and cancer cachexia. These findings are incorporated herein by reference, and as an example, one set of this data is presented here.

Applicants tested the ability of ActRIIB (R64 20-134)-mFc to attenuate muscle loss in a mouse model of glucocorticoid-induced muscle wasting.

Mice were subcutaneously dosed daily for 13 days with either PBS or dexamethasone (2 mg/kg) to induce muscle wasting. Over the same 13 days, PBS- and dexamethosone-treated groups received vehicle or ActRIIB (R64 20-134)-mFc (10 mg/kg; i.p.; twice/week) such that all combinations of treatments were represented. Mice were NMR scanned at days 0 and 13 to determine changes in lean tissue mass across the groups. NMR results are outlined in Table 6, below.

TABLE 6

Lean tissue mass of vehicle- and murine ActRIIB (R64 20-134)-Fc-treated mice

| Group (sc:ip treatment) | Avg lean day 13-Avg lean day 0 (g) ± std dev |
|---|---|
| PBS:PBS | 0.83 ± 0.94 |
| Dexameth:PBS | 0.47 ± 0.34[a] |
| Dexameth:ActRIIB | 2.56 ± 0.37[a,b] |
| PBS:ActRIIB | 3.63 ± 0.62[a] |

[a]Significant difference compared to PBS:PBS at $p < 0.05$
[b]Significant difference compared to Dexameth:PBS at $p < 0.05$ NMR scanning showed a significant 2.5% decrease in lean tissue mass in the dexamethasone:PBS group compared to the PBS:PBS cohort. In contrast, the dexamethasone:ActRIIB (R64 20-134)-mFc group exhibited a 13.5% increase in lean tissue mass, a significant increase when compared to both the PBS:PBS and the dexamethasone:PBS groups. Cachexia is an undesirable side effect for a variety of therapeutic treatments, including chronic glucocorticoid therapy. Therefore it could be of clinical importance that treatment with a human ActRIIB (R64 20-134)-mFc protein can attenuate the muscle wasting associated with cachexia.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

I claim:

1. A follistatin fusion protein comprising a first amino acid sequence and a second amino acid sequence, wherein the first amino acid sequence comprises a sequence that is at least 90% identical to SEQ ID NO: 17 or that is at least 90% identical to a mature form of SEQ ID NO: 17, and wherein the second amino acid sequence comprises an immunoglobulin Fc domain; wherein the fusion protein comprises a linker between the first amino acid sequence and the second amino acid sequence; and wherein the linker comprises three glycines.

2. The follistatin fusion protein of claim 1, wherein the first amino acid sequence comprises a sequence that is at least 95% identical to SEQ ID NO: 17, or that is at least 95% identical to a mature form of SEQ ID NO: 17.

3. The follistatin fusion protein of claim 1, wherein the immunoglobulin Fc domain is selected from the group consisting of: an IgG1 Fc domain, an IgG2 Fc domain, an IgG3 Fc domain and an IgG4 Fc domain.

4. The follistatin fusion protein of claim 1, wherein the linker further comprises a threonine.

5. The follistatin fusion protein of claim 4, wherein the linker is 4 amino acids in length.

6. The follistatin fusion protein of claim 5, wherein the first amino acid sequence comprises the amino acid sequence of SEQ ID NO: 17.

7. The follistatin fusion protein of claim 6, wherein the immunoglobulin Fc domain is an IgG2 Fc domain.

8. The follistatin fusion protein of claim 5, wherein the first amino acid sequence comprises a mature form of the amino acid sequence of SEQ ID NO: 17.

9. The follistatin fusion protein of claim 1, wherein the linker is 4 amino acids in length.

10. The follistatin fusion protein of claim 1, wherein the first amino acid sequence comprises a sequence that is at least 97% identical to SEQ ID NO: 17 or that is at least 97% identical to a mature form of SEQ ID NO: 17.

11. The follistatin fusion protein of claim 10, wherein the linker is 50 or more amino acids in length.

12. The follistatin fusion protein of claim 11, wherein the immunoglobulin Fc domain is an IgG1 Fc domain.

13. The follistatin fusion protein of claim 12, wherein the first amino acid sequence comprises the amino acid sequence of SEQ ID NO: 17.

14. The follistatin fusion protein of claim 12, wherein the first amino acid sequence comprises a mature form of the amino acid sequence of SEQ ID NO: 17.

15. The follistatin fusion protein of claim 11, wherein the first amino acid sequence comprises the amino acid sequence of SEQ ID NO: 17.

16. The follistatin fusion protein of claim 11, wherein the first amino acid sequence comprises a mature form of the amino acid sequence of SEQ ID NO: 17.

17. The follistatin fusion protein of claim 1, wherein the first amino acid sequence comprises the amino acid sequence of SEQ ID NO: 17 or a mature form of SEQ ID NO: 17.

18. The follistatin fusion protein of claim 1, wherein the first amino acid sequence comprises an N-terminal follistatin domain (FSND) having the amino acid sequence of SEQ ID NO: 18.

19. The follistatin fusion protein of claim 18, wherein the first amino acid sequence comprises a first follistatin domain (FSD1) having the amino acid sequence of SEQ ID NO: 20.

20. The follistatin fusion protein of claim 18, wherein the first amino acid sequence comprises a second follistatin domain (FSD2) having the amino acid sequence of SEQ ID NO: 19.

21. The follistatin fusion protein of claim 1, wherein the linker is 50 or more amino acids in length.

22. The follistatin fusion protein of claim 1, wherein the immunoglobulin Fc domain is an IgG2 Fc domain.

23. A pharmaceutical composition comprising the fusion protein of claim 1.

* * * * *

SEQUENCE LISTING

<160> NUMBER OF SEQ ID NOS: 25

<210> SEQ ID NO 1
<211> LENGTH: 512
<212> TYPE: PRT
<213> ORGANISM: Homo sapiens

<400> SEQUENCE: 1

```
Met Thr Ala Pro Trp Val Ala Leu Ala Leu Leu Trp Gly Ser Leu Trp
 1               5                  10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335
```

```
Leu Ala Asp Phe Gly Leu Ala Val Arg Phe Glu Pro Gly Lys Pro Pro
                340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
        370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30
```

Glu Gln Asp Lys Arg Leu His Cys Tyr Ala Ser Trp Ala Asn Ser Ser
          35                  40                  45
Gly Thr Ile Glu Leu Val Lys Lys Gly Cys Trp Leu Asp Asp Phe Asn
 50                  55                  60
Cys Tyr Asp Arg Gln Glu Cys Val Ala Thr Glu Glu Asn Pro Gln Val
 65                  70                  75                  80
Tyr Phe Cys Cys Cys Glu Gly Asn Phe Cys Asn Glu Arg Phe Thr His
                 85                  90                  95
Leu Pro Glu Ala
        100

<210> SEQ ID NO 4
<211> LENGTH: 1539
<212> TYPE: DNA
<213> ORGANISM: Homo sapiens

<400> SEQUENCE: 4

| | | | | | |
|---|---|---|---|---|---|
| atgacggcgc | cctgggtggc | cctcgccctc | ctctggggat | cgctgtgcc | cggctctggg | 60 |
| cgtggggagg | ctgagacacg | ggagtgcatc | tactacaacg | ccaactggga | gctggagcgc | 120 |
| accaaccaga | gcggcctgga | cgctgcgaa | ggcgagcagg | acaagcggct | gcactgctac | 180 |
| gcctcctggg | ccaacagctc | tggcaccatc | gagctcgtga | agaagggctg | ctggctagat | 240 |
| gacttcaact | gctacgatag | gcaggagtgt | gtggccactg | aggagaaccc | ccaggtgtac | 300 |
| ttctgctgct | gtgaaggcaa | cttctgcaac | gagcgcttca | ctcatttgcc | agaggctggg | 360 |
| ggccccggaag | tcacgtacga | gccacccccg | acagccccca | ccctgctcac | ggtgctggcc | 420 |
| tactcactgc | tgcccatcgg | gggccttttcc | ctcatcgtcc | tgctggcctt | ttggatgtac | 480 |
| cggcatcgca | agcccccta | cggtcatgtg | gacatccatg | aggaccctgg | gcctccacca | 540 |
| ccatcccctc | tggtgggcct | gaagccactg | cagctgctgg | agatcaaggc | tcggggcgc | 600 |
| tttggctgtg | tctggaaggc | ccagctcatg | aatgactttg | tagctgtcaa | gatcttccca | 660 |
| ctccaggaca | agcagtcgtg | gcagagtgaa | cgggagatct | tcagcacacc | tggcatgaag | 720 |
| cacgagaacc | tgctacagtt | cattgctgcc | gagaagcgag | gctccaacct | cgaagtagag | 780 |
| ctgtggctca | tcacggcctt | ccatgacaag | ggctcccctca | cggattacct | caaggggaac | 840 |
| atcatcacat | ggaacgaact | gtgtcatgta | gcagagacga | tgtcacgagg | cctctcatac | 900 |
| ctgcatgagg | atgtgccctg | gtgccgtggc | gagggccaca | gccgtctat | tgcccacagg | 960 |
| gacttttaaaa | gtaagaatgt | attgctgaag | agcgacctca | cagccgtgct | ggctgacttt | 1020 |
| ggcttggctg | ttcgatttga | gccagggaaa | cctccagggg | acacccacgg | acaggtaggc | 1080 |
| acgagacggt | acatggctcc | tgaggtgctc | gagggagcca | tcaacttcca | gagagatgcc | 1140 |
| ttcctgcgca | ttgacatgta | tgccatgggg | ttggtgctgt | gggagcttgt | gtctcgctgc | 1200 |
| aaggctgcag | acggacccgt | ggatgagtac | atgctgccct | ttgaggaaga | gattggccag | 1260 |
| caccttcgt | tggaggagct | gcaggaggtg | gtggtgcaca | agaagatgag | gcccaccatt | 1320 |
| aaagatcact | ggttgaaaca | cccgggcctg | gcccagcttt | gtgtgaccat | cgaggagtgc | 1380 |
| tgggaccatg | atgcagaggc | tcgcttgtcc | gcgggctgtg | tggaggagcg | ggtgtccctg | 1440 |
| attcggaggt | cggtcaacgg | cactacctcg | gactgtctcg | tttccctggt | gacctctgtc | 1500 |
| accaatgtgg | acctgccccc | taaagagtca | agcatctaa | | | 1539 |

<210> SEQ ID NO 5
<211> LENGTH: 348
<212> TYPE: DNA

<213> ORGANISM: Homo sapiens

<400> SEQUENCE: 5

```
tctgggcgtg gggaggctga gacacgggag tgcatctact acaacgccaa ctgggagctg      60
gagcgcacca accagagcgg cctggagcgc tgcgaaggcg agcaggacaa gcggctgcac     120
tgctacgcct cctgggccaa cagctctggc accatcgagc tcgtgaagaa gggctgctgg     180
ctagatgact tcaactgcta cgataggcag gagtgtgtgg ccactgagga gaacccccag     240
gtgtacttct gctgctgtga aggcaacttc tgcaacgagc gcttcactca tttgccagag     300
gctgggggcc cggaagtcac gtacgagcca cccccgacag ccccccacc                 348
```

<210> SEQ ID NO 6
<211> LENGTH: 344
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
```

```
                275                 280                 285
Lys Thr Thr Pro Pro Val Leu Asp Ser Asp Gly Ser Phe Phe Leu Tyr
        290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 7
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (44)..(44)
<223> OTHER INFORMATION: Asp or Ala
<220> FEATURE:
<221> NAME/KEY: MOD_RES
<222> LOCATION: (102)..(102)
<223> OTHER INFORMATION: Lys or Ala
<220> FEATURE:
<221> NAME/KEY: MOD_RES
<222> LOCATION: (215)..(215)
<223> OTHER INFORMATION: Asn or Ala

<400> SEQUENCE: 7

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Xaa Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Xaa Val Ser Asn Lys Ala Leu Pro Val Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Pro Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Xaa His Tyr Thr Gln Lys Ser Leu Ser Leu
    210                 215                 220
```

Ser Pro Gly Lys
225

<210> SEQ ID NO 8
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 9
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys

<210> SEQ ID NO 10
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg caccatcga gctcgtgaag      240
aagggctgct ggctagatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc accccccgac agcccccacc     420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gtccccatcg agaaaaccat ctccaaagcc     780
aaagggcagc cccgagaacc acaggtgtac accctgcccc catcccggga ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctggac     960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaatga                                         1107
```

<210> SEQ ID NO 11
<211> LENGTH: 21
<212> TYPE: PRT
<213> ORGANISM: Apis sp.

<400> SEQUENCE: 11

Met Lys Phe Leu Val Asn Val Ala Leu Val Phe Met Val Val Tyr Ile
1               5                   10                  15
Ser Tyr Ile Tyr Ala
            20

<210> SEQ ID NO 12
<211> LENGTH: 22
<212> TYPE: PRT
<213> ORGANISM: Unknown
<220> FEATURE:
<223> OTHER INFORMATION: Description of Unknown: Tissue plasminogen activator leader sequence

<400> SEQUENCE: 12

Met Asp Ala Met Lys Arg Gly Leu Cys Cys Val Leu Leu Leu Cys Gly
1               5                   10                  15

```
Ala Val Phe Val Ser Pro
            20

<210> SEQ ID NO 13
<211> LENGTH: 20
<212> TYPE: PRT
<213> ORGANISM: Unknown
<220> FEATURE:
<223> OTHER INFORMATION: Description of Unknown: Native leader sequence

<400> SEQUENCE: 13

Met Gly Ala Ala Ala Lys Leu Ala Phe Ala Val Phe Leu Ile Ser Cys
1               5                   10                  15

Ser Ser Gly Ala
            20

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Gly Gly Gly Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly Gly Gly Gly
1               5

<210> SEQ ID NO 16
<211> LENGTH: 343
<212> TYPE: PRT
<213> ORGANISM: Homo sapiens

<400> SEQUENCE: 16

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
            115                 120                 125
```

```
Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
290                 295                 300

Gly Val Leu Leu Glu Val Lys His Gly Ser Cys Asn Ser Ile Ser Glu
305                 310                 315                 320

Asp Thr Glu Glu Glu Glu Asp Glu Asp Gln Asp Tyr Ser Phe Pro
                325                 330                 335

Ile Ser Ser Ile Leu Glu Trp
            340

<210> SEQ ID NO 17
<211> LENGTH: 317
<212> TYPE: PRT
<213> ORGANISM: Homo sapiens

<400> SEQUENCE: 17

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160
```

```
Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315

<210> SEQ ID NO 18
<211> LENGTH: 63
<212> TYPE: PRT
<213> ORGANISM: Homo sapiens

<400> SEQUENCE: 18

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys
    50                  55                  60

<210> SEQ ID NO 19
<211> LENGTH: 25
<212> TYPE: PRT
<213> ORGANISM: Homo sapiens

<400> SEQUENCE: 19

Glu Thr Cys Glu Asn Val Asp Cys Gly Pro Gly Lys Lys Cys Arg Met
1               5                   10                  15

Asn Lys Lys Asn Lys Pro Arg Cys Val
            20                  25

<210> SEQ ID NO 20
<211> LENGTH: 26
<212> TYPE: PRT
<213> ORGANISM: Homo sapiens

<400> SEQUENCE: 20

Lys Thr Cys Arg Asp Val Phe Cys Pro Gly Ser Ser Thr Cys Val Val
1               5                   10                  15

Asp Gln Thr Asn Asn Ala Tyr Cys Val Thr
            20                  25
```

```
<210> SEQ ID NO 21
<211> LENGTH: 262
<212> TYPE: PRT
<213> ORGANISM: Homo sapiens

<400> SEQUENCE: 21

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Val Pro Ser Ser Pro Gly Gln Glu
        195                 200                 205

Leu Cys Gly Asn Asn Asn Val Thr Tyr Ile Ser Ser Cys His Met Arg
    210                 215                 220

Gln Ala Thr Cys Phe Leu Gly Arg Ser Ile Gly Val Arg His Ala Gly
225                 230                 235                 240

Ser Cys Ala Gly Thr Pro Glu Glu Pro Pro Gly Gly Glu Ser Ala Glu
                245                 250                 255

Glu Glu Glu Asn Phe Val
            260

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Arg Gly Glu Ala Glu
1               5

<210> SEQ ID NO 23
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 116
<212> TYPE: PRT
<213> ORGANISM: Homo sapiens

<400> SEQUENCE: 24

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Thr
            115

<210> SEQ ID NO 25
<211> LENGTH: 115
<212> TYPE: PRT
<213> ORGANISM: Homo sapiens

<400> SEQUENCE: 25

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
                100                 105                 110

Ala Pro Thr
        115
```